US009137958B2

(12) United States Patent
Elliott et al.

(10) Patent No.: US 9,137,958 B2
(45) Date of Patent: Sep. 22, 2015

(54) TOBACCO HAVING ALTERED AMOUNTS OF ENVIRONMENTAL CONTAMINANTS

(75) Inventors: Patsy Elizabeth Elliott, Winston-Salem, NC (US); Darlene Madeline Lawson, Kernersville, NC (US)

(73) Assignee: Reynolds Technologies, Inc., Winston-Salem, NC (US)

( * ) Notice: Subject to any disclaimer, the term of this patent is extended or adjusted under 35 U.S.C. 154(b) by 627 days.

(21) Appl. No.: 13/368,797

(22) Filed: Feb. 8, 2012

(65) Prior Publication Data

US 2013/0199553 A1    Aug. 8, 2013

(51) Int. Cl.
| | | |
|---|---|---|
| *A24B 13/00* | (2006.01) | |
| *A01H 5/12* | (2006.01) | |
| *C12N 15/00* | (2006.01) | |
| *A24B 15/24* | (2006.01) | |
| *A01H 1/06* | (2006.01) | |
| *A01H 1/04* | (2006.01) | |
| *A24B 15/20* | (2006.01) | |
| *C12N 15/01* | (2006.01) | |

(52) U.S. Cl.
CPC .. *A01H 1/06* (2013.01); *A01H 1/04* (2013.01); *A01H 5/12* (2013.01); *A24B 15/20* (2013.01); *A24B 15/248* (2013.01); *C12N 15/01* (2013.01)

(58) Field of Classification Search
None
See application file for complete search history.

(56) References Cited

U.S. PATENT DOCUMENTS

| | | | |
|---|---|---|---|
| 3,772,516 A | 11/1973 | Roberts et al. | |
| 4,407,307 A | 10/1983 | Gaisch et al. | |
| 4,537,204 A | 8/1985 | Gaisch et al. | |
| 5,539,093 A | 7/1996 | Fitzmaurice et al. | |
| 5,668,295 A | 9/1997 | Wahab et al. | |
| 5,670,349 A | 9/1997 | Cramer et al. | |
| 5,705,624 A | 1/1998 | Fitzmaurice et al. | |
| 5,741,898 A | 4/1998 | Hanley et al. | |
| 5,819,751 A | 10/1998 | Barnes et al. | |
| 5,837,876 A | 11/1998 | Conkling et al. | |
| 6,030,462 A | 2/2000 | Shu et al. | |

(Continued)

FOREIGN PATENT DOCUMENTS

| | | |
|---|---|---|
| WO | WO 98/56923 | 12/1998 |
| WO | WO 01/16144 A2 | 3/2001 |

(Continued)

OTHER PUBLICATIONS

Cattoir-Reynaerts et al, (1983), Selection and Characterization of Carrot Embryoid Cultures Resistant to Inhibition by Lysine Plus Threonine, Biochem. Physiol. Pflanzen, 178: 81-90.

(Continued)

*Primary Examiner* — Anne Kubelik
*Assistant Examiner* — Ashley K Buran
(74) *Attorney, Agent, or Firm* — Kilpatrick Townsend & Stockton LLP

(57) ABSTRACT

Disclosed herein are genetically modified tobacco plants, and tobacco products derived from such plants, comprising an altered uptake and/or altered levels of at least one environmental contaminant or other non-natural chemical as compared to an unmodified parent tobacco plant from which the modified plant is derived. The alteration in uptake and/or levels may be a reduction, or alternatively an increase, in the uptake and/or levels of the environmental contaminant or other non-natural chemical. These methods and plants are useful for improving tobacco products or in generating tobacco lines that may have environmentally useful properties.

12 Claims, 2 Drawing Sheets

(56) References Cited

U.S. PATENT DOCUMENTS

| | | | |
|---|---|---|---|
| 6,730,832 | B1 | 5/2004 | Dominguez et al. |
| 7,173,170 | B2 | 2/2007 | Liu et al. |
| 7,825,305 | B2 | 11/2010 | Dominguez et al. |
| 8,716,571 | B2* | 5/2014 | Elliott et al. ............... 800/317.3 |
| 2006/0185686 | A1 | 8/2006 | Lawrence, Jr. |
| 2007/0006888 | A1 | 1/2007 | Hicks et al. |
| 2009/0123626 | A1 | 5/2009 | Rommens et al. |
| 2010/0136169 | A1 | 6/2010 | Van Der Laan et al. |
| 2011/0023178 | A1 | 1/2011 | Dominguez et al. |
| 2011/0048434 | A1 | 3/2011 | Chen et al. |
| 2011/0174323 | A1 | 7/2011 | Coleman, III et al. |

FOREIGN PATENT DOCUMENTS

| | | |
|---|---|---|
| WO | WO 02/100199 | 12/2002 |
| WO | WO 2009/074325 A1 | 6/2009 |
| WO | WO 2009/074329 | 6/2009 |
| WO | WO 2012/028309 A2 | 3/2012 |
| WO | WO 2012/041913 | 4/2012 |

OTHER PUBLICATIONS

Dotson et al, (1990), Lysine-Insensitive Aspartate Kinase in Two Threonine-Overproducing Mutants of Maize, Planta, 182: 546-552.
Ellstrand, (2001), When transgenes wander, should we worry?, Plant Physiol., 125: 1543-1545.
Bright et al., (1982), Two Genes for Threonine Accumulation in Barley Seeds, Nature, 299:278-279.
Chen et al., (1999), Comparison of volatile generation in serine/threonine/glutamine-ribose/glucose/fructose model system, J. Agric. Food Chem., 47: 643-647.
Currin et al., (1981), Registration of Clemson PD4 Flue-Cured Tobacco, Copr Sci., 21:988.
Falco, S. et al., (1995), Transgenic canola and soybean seeds with increased lysine, Biotechnology 13: 577-582.
Falco, S. et al., (1997), Using bacterial genes to engineer plants with increased seed lysine, SIM News 47:53-57.
Galili et al., (1999), Enhancing the Content of Essential Amino Acids Lysine and Threonine in Plants, In: Plant Amino Acids in Biochemistry and Biotechnology, B.K. Singh, ed., Marcel Dekker, New York, pp. 487-507.
Hibberd et al, (1980), Selection and Characterization of a Feedback-Insensitive Tissue Culture of Maize, Planta, 148: 183-187.
Imsande, (2001), Selection of Soybean Mutants with Increased Concentrations of Seed Methionine and Cysteine, Crop Sci., 41:510-515.
Karchi, H. et al., (1993), Seed-specific expression of a bacterial desensitized aspartate kinase increases the production of seed threonine and methionine in transgenic tobacco, Plant J., 3: 721-727.
Lea et al., (1985), The Biosynthesis of Amino Acids in Plant, In: Chemistry and Biochemistry o f the Amino Acids, G.C. Barrett, ed.. Chapman & Hill , London, pp. 197-226.
Lu, G. et. Al., (1997), Generation of Flavor Compounds by the Reaction of 2-Deoxyglucose with Selected Amino Acids, J. Agric. Food Chem., 45: 233-236.
Moldoveanu et al., (2011), Acrylamide analysis in tobacco, alternative tobacco products, and cigarette smoke, J. Chromatogr. Sci., 49: 234-242.
Shaul, O. et al., (1992), Threonine Overproduction in Transgenic Tobacco Plants Expressing a Mutant Desensitized Aspartate Kinase of *Escherichia coli*., Plant Physiol, 100:1157-1163.
Van Harten, Mutation Breeding: Theory and Practical Applications, pp. 1-63, Cambridge Univ. Press, New York, N.Y., 1998.
Williams et al., (1968), Changes in Amino Acid Content of Flue Cured Tobacco During Natural Aging, Tobacco Science, 128:243-247.
Bright et al., (1982), Threonine Accumulation in the Seeds of a Barley Mutant with an Altered Kinase, Biochem. Genet., 20:229-243.
Broun et al., (2001), Progress in Plant Metabolic Engineering, PNAS, 98:8925-8927.
Diedrick et al., (1990), Tissue Culture Isolation of a Second Mutant Locus for Increased Threonine Accumulation in Maize, Theor. Appl. Genet., 79:209-215.
Fehr, (1983), Mutation Breeding, in Applied Plant Breeding, Chapter 6, pp. 6-1 to 6-30, $2^{nd}$ Edition Iowa State University, Ames, IA.
Frankard et al., (1991), High Threonine Producer Mutant of *Nicotiana sylvestris* (spegg. And comes), Theor. Appl. Genet., 82:273-282.
Frankard et al., (1992), Two Feedback-Insensitive Enzymes of the Aspartate Pathway in *Nicotiana sylvestris*, Plant Physiol., 99:1285-1293.
Galili, (1995), Regulation of Lysine and Threonine Synthesis, The Plant Cell, 7: 899-906.
Haughn, et al., (1987), Selection for Herbicide Resistance at the Whole Plant Level, in: Biotechnology in Agricultural Chemistry, H. M. Lebaron (ed.), American Chemical Society, Washington, D.C., pp. 98-107.
Heremans, et al., (1995), Threonine Accumulation in a Mutant of *Arabidopsis thaliana* (L.) Heynh, with an Altered Aspartate Kinase, J. Plant Physiol., 146: 249-257.
Lugon-Moulin, et al., (2006), Cadmium concentration in tobacco (*Nicotiana tabacum* L.) from different countries and its relationship with other elements, Chemosphere. 63(7):1074-86. Epub 2005.
Lugon-Moulin, et al., (2006), Cadmium content of phosphate fertilizers used for tobacco production, Agron. Sustain. Dev, 26:151-156.
Malmberg et al., (1993), Chapter 2; Production and Analysis of Plant Mutants, Emphasizing *Arabidopsis thaliana*, in: Methods in Plant Molecular Biology and Biotechnology, B. R. Glick and 1E. Thompson, (eds.), CRC press.
Matthews, (1999), Lysine, Threonine and Methionine Biosynthesis, in: PlantAmino Acids Biochemistry and Biotechnology, B. K. Singh, (ed.), Marcel Dekker, Inc., New York, pp. 205-225.
Peng, et al., (1993), Derivative Alleles of the *Arabidopsis* Gibberellin-Insensitive (gai) Mutation Confer a Wild-Type Phenotype, The Plant Cell, 5: 351-360 (1993).
Adamu, et al., (1989), Residual metal concentrations in soils and leaf accumulations in tobacco a decade following farmland application of municipal sludge, Environ Pollut., 56(2):113-26.
Lee, et al., (2003), Functional expression of a bacterial heavy metal transporter in *Arabidopsis* enhances resistance to and decreases uptake of heavy metals, Plant Physiol., 133(2):589-96. Epub 2003.
Wagner et al., (1986), Variation in cadmium accumulation potential and tissue distribution of cadmium in tobacco, Plant Physiol., 82(1):274-9.
Bourgin, J. et al., Valine-resistance, a potential marker in plant call genetics. I. Distinction between two types of valine-resistant tobacco mutants isolated from protoplast-derived cells, Genetics, vol. 109, pp. 393-470, 1985.
Lea, P. et al., Asparagine in Plants, Annuals of Applied Biology, vol. 150, pp. 1-26, 2007.
United States Patent and Trademark Office, Office Action, U.S. Appl. No. 13/238,181, mailed Jun. 28, 2013.
United States Patent and Trademark Office, Office Action, U.S. Appl. No. 12/804,617, mailed Mar. 14, 2014.
Kaye, C. et al., Constitutive non-inducible expression of the *Arabidopsis thaliana* Nia 2 gene in Two Nitrate Reductase Mutants of *Nicotiana plumbaginifolia*, Plant Molec. Biol., 33:953-964, 1997.
Lea, P. et al., Asparagine in Plants, Annals App. Biol., 150:1-26, 2006.
Lea, U. et al., Posttranslational Regulation of Nitrate Reductase Strongly Affects the Levels of Free Amino Acids and Nitrate, whereas Transcriptional Regulation has only Minor Influence, Plant Physiology, 140:1085-1094, 2006.
Matt, P. et al., Decreased Rubisco Activity leads to Dramatic Changes of Nitrate Metabolism, Amino Acid Metabolism and the Levels of Phenylpropanoids and Nicotine in Tobacco Antisense RBCS Transformants, Plant J., 30:663-677, 2002.
Olesen, P. et al., Acrylamide Exposure and Incidence of Breast Cancer among Postmenopausal Women in the Danish Diet, Cancer and Health Study, Int. J. Cancer, 122:2094-2100, 2008.
Rommens, C. et al., Intragenic Crop Improvements: Combining the Benefits of Traditional Breeding and Genetic Engineering, J. Agric. Food Chem., 55:4281-4288, 2007.

(56) References Cited

OTHER PUBLICATIONS

Rousselin, P. et al., Characterization of Three Hormone Mutants of *Nicotiana plumbaginifolia*: Evidence for a Common ABA Deficiency, Theor. Appl. Genet., 85:213-221, 1992.

Zyzak, D. et al., Acrylamide Formation Mechanism in Heated Foods, J. Agric. Food Chem., 51:4782-4787, 2003.

Devi, S. et al., Isolation of aluminum-tolerant cell lines of tobacco in a simple calcium medium and their responses to aluminum, Physiol. Plant, 112(3):397-402, 2001.

Howden, R., Cadmiun-sensitive mutants of a *Arabidopsis thaliana*, Plant Physiol., 100(1):100-107, 1992.

Patent Cooperation Treaty, International Search Report and Written Opinion, International Application No. PCT/US2013/024730, mailed May 6, 2013.

Patent Cooperation Treaty, International Search Report and Written Opinion, International Application No. PCT/US12/56303, mailed Nov. 23, 2013.

United States Patent and Trademark Office, Notice of Allowance and Fees Due, U.S. Appl. No. 12/804,617, mailed Dec. 17, 2014.

European Patent Office, Extended Search Resport, European Application No. 12834296.1, mailed Dec. 19, 2014.

United States Patent and Trademark Office, Notice of Allowance and Fees Due, U.S. Appl. No. 13/238,181, mailed Dec. 16, 2013.

* cited by examiner

US 9,137,958 B2

TOBACCO HAVING ALTERED AMOUNTS OF ENVIRONMENTAL CONTAMINANTS

FIELD OF THE INVENTION

The present invention relates methods for making tobacco having altered amounts of at least one environmental contaminant, such as a heavy metal, and tobacco lines produced by such methods.

BACKGROUND OF THE INVENTION

Popular smoking articles, such as cigarettes, may have a substantially cylindrical rod shaped structure and include a charge, roll or column of smokeable material such as shredded tobacco (e.g., in cut filler form) surrounded by a paper wrapper. Also, tobacco may be used for smokeless products such as chewing tobacco and other smokeless tobacco products. For example, various types of smokeless tobacco products are set forth in U.S. Patent Publication No. 2011/0048434 the disclosure of which is incorporated by reference herein in its entirety.

Throughout the years, various methods have been developed to improve the flavor of tobacco and tobacco products. In addition to improving flavor, it would be helpful to produce tobacco plants, and tobacco products derived from such plants, having reduced amounts of certain potentially toxic chemicals. For example, it would be of interest to produce tobacco plants and tobacco products having reduced heavy metals.

Cadmium (Cd) is a heavy metal that can be found in soils. In the field, phosphate fertilizers can be a source of cadmium and the concentration can vary based on agricultural practices, soil characteristics, climate and plant varieties (Lugon-Moulin et al., Agronomy for Sustainable Development, 26:151-156, 2006). Cadmium can accumulate in tobacco. Studies indicate that stalk position, crop year and growing region may have an effect on cadmium content. Also, due to differing climates and soils, establishment of true genetic differences in existing cultivars may be difficult to characterize with precision (Lugon-Moulin et al., Chemosphere, 63: 1074-1086, 2006). For example, studies indicate that potential cadmium accumulation differences may exist between the *Nicotiana* species but less so within varieties of *Nicotiana tabacum* (Wagner and Yeargan, Plant Physiology, 82: 274-279, 1986).

Since tobacco (e.g., lamina, stems, flowers and roots) is used in the manufacturing of cigarettes and alternative tobacco products, developing new cultivars that less effectively translocate heavy metals such as cadmium from roots to shoots may be beneficial.

Also, as tobacco can take up such environmental contaminants, tobacco lines that take up an increased amount of such compounds may be used to decrease the amount of such chemicals in soil (e.g., for soil clean-up).

Thus, there is a general need for methods that can provide plant lines comprising altered uptake of a heavy metal contaminant or other non-natural chemicals, or other compounds from the environment, where such compounds may be potentially toxic if ingested over long periods of time. The method should be designed so that even for plant species such as tobacco that have a complex genome and thus require screening of a large number of mutation events to isolate the mutation of interest, and that are large and thus require extensive facilities for breeding, screening for the desired phenotype is economical.

SUMMARY OF THE INVENTION

The present invention provides tobacco plants having significantly altered uptake and/or altered levels of at least one environmental contaminant or other non-natural chemicals and methods of making such plants.

In certain embodiments, the present invention provides methods of making tobacco plants or a portion thereof having significantly altered uptake and/or altered levels of at least one environmental contaminant or other non-natural chemicals as compared to an unmodified tobacco plant or portion thereof from which the modified plant is derived. The alteration in uptake and/or levels may be a reduction in the uptake and/or levels of the at least one environmental contaminant or other non-natural chemicals as compared to an unmodified tobacco plant or portion thereof from which the modified plant is derived. Or, the alteration in uptake and/or levels may be an increase in the uptake and/or levels of the at least one environmental contaminant or other non-natural chemicals as compared to an unmodified tobacco plant or portion thereof from which the modified plant is derived.

In certain embodiments, the method for producing a modified tobacco plant or a portion thereof comprising altered uptake and/or altered levels of at least one environmental contaminant or other non-natural chemical as compared to an unmodified tobacco plant or portion thereof from which the modified plant is derived may comprise the steps of: incubating seeds from the unmodified tobacco plant in a solution comprising a mutagen; washing the seeds free of the mutagen; germinating the seeds and growing M0 tobacco seedlings in the presence of a selection agent to generate at least one M0 tobacco plant comprising M1 tobacco seeds, wherein the M1 tobacco seeds comprise at least one mutagenized M1 tobacco seed; and germinating the at least one mutagenized M1 tobacco seed to select for a modified M1 tobacco plant or a portion thereof comprising altered uptake and/or altered levels of at least one environmental contaminant or other non-natural chemical. In certain embodiments, the method may comprise germinating the M1 plants (and/or M2 and/or M3 and/or M4 plants and/or subsequent generations) derived from the M0 plants in a medium comprising a selection agent.

In yet other embodiments, the invention comprises a modified tobacco plant or a portion thereof comprising altered uptake and/or altered levels of at least one environmental contaminant or other non-natural chemical as compared to an unmodified tobacco plant or portion thereof from which the modified plant is derived. The alteration in uptake and/or levels may be a reduction in the uptake and/or levels of the at least one environmental contaminant or other non-natural chemicals as compared to an unmodified tobacco plant or portion thereof from which the modified plant is derived. Or, the alteration in uptake and/or levels may be an increase in the uptake and/or levels of the at least one environmental contaminant or other non-natural chemicals as compared to an unmodified tobacco plant or portion thereof from which the modified plant is derived.

In certain embodiments, the present invention comprises a tobacco plant derived from one of the tobacco lines described herein. For example, in certain embodiments, the invention may comprise a tobacco plant comprising at least one of the 10TN-278-2, 10TN-253-4, 10TN-256-1 or 10TN-287-4 lines.

Also, in some embodiments, the present invention comprises tobacco products made from the plants and tobacco lines of the invention. For example, in certain embodiments, the present invention comprises tobacco products comprising a modified tobacco having decreased uptake and/or reduced levels of at least one environmental contaminant or other non-natural chemical as compared to tobacco from an unmodified tobacco plant or portion thereof from which the modified plant is derived.

In certain embodiments, the present invention comprises a composition (e.g., a tobacco product) comprising tobacco derived from one of the tobacco lines described herein. For example, in certain embodiments, the invention may comprise a composition comprising at least one of the 10TN-278-2, 10TN-253-4, 10TN-256-1 or 10TN-287-4 lines.

In each of the embodiments of the invention, the environmental contaminant or other non-natural chemical having altered uptake may comprise a heavy metal. The heavy metal may be at least one of arsenic (As), cadmium (Cd), chromium (Cr), nickel (Ni), lead (Pb), selenium (Se), zinc (Zn), copper (Cu), mercury (Hg) or silver (Ag). In an embodiment, the heavy metal having altered uptake and/or levels is cadmium. Or, other heavy metals and/or other selected elements may be reduced.

BRIEF DESCRIPTION OF THE DRAWINGS

Various features, aspects, and advantages of the present invention will become more apparent with reference to the following description, appended claims, and accompanying drawings.

DETAILED DESCRIPTION

Definitions

Figure 1:
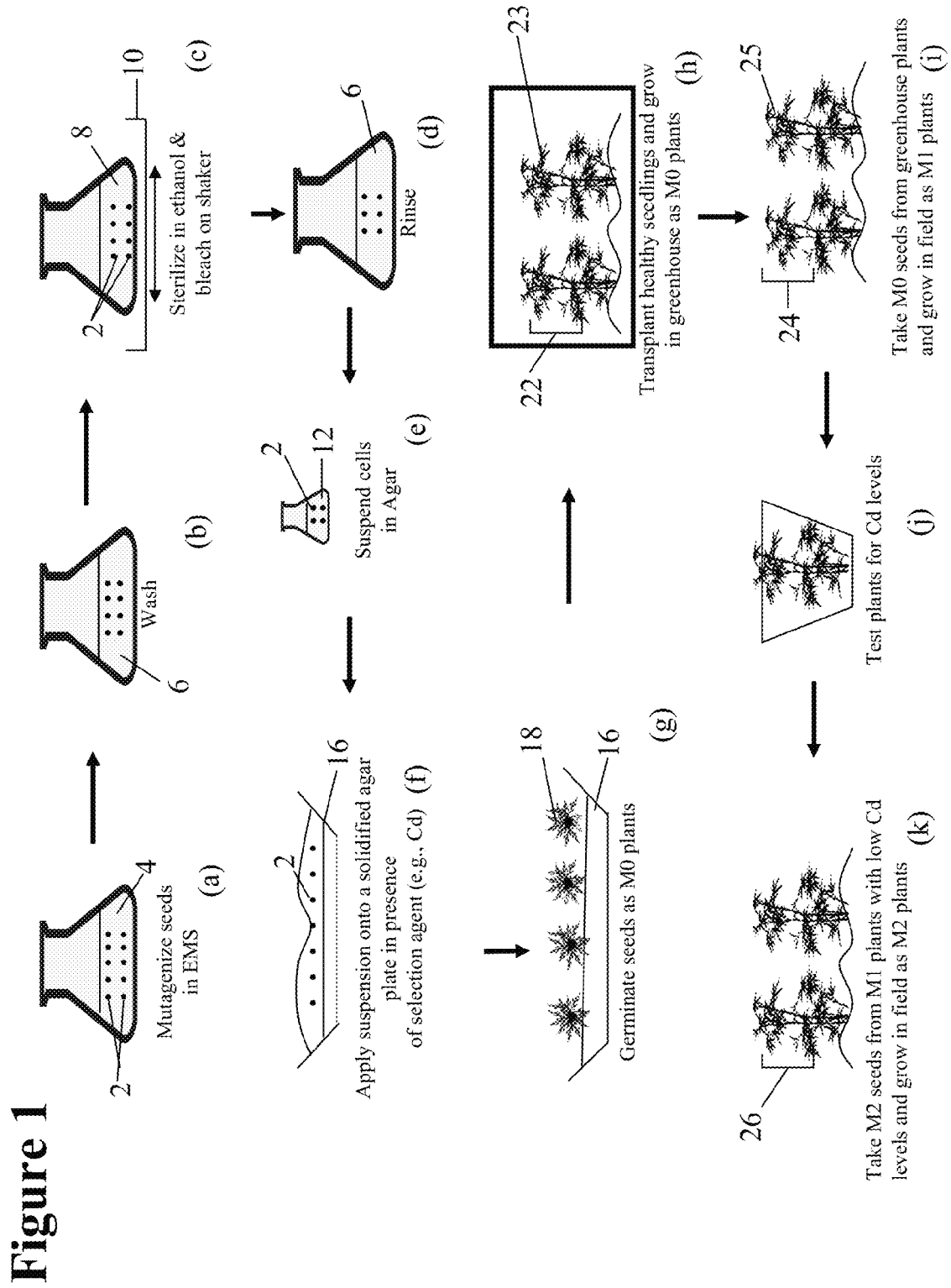
FIG. 1 is a schematic representation illustrating a method for generating tobacco lines with altered levels of at least one environmental contaminant or other non-natural chemical according to one embodiment of the invention.

As used in this specification and the claims, the singular forms "a," "an," and "the" include plural referents unless the context clearly dictates otherwise. Also the terms "seed(s)" and "seedling(s)" include single and plural referents.

Reference to "dry weight percent" or "dry weight basis" refers to weight on the basis of dry ingredients (i.e., all ingredients except water).

The term "non-natural" refers to compounds that are not naturally ingested by animals and/or taken up and/or synthesized in the plant being modified by the methods of the invention (e.g., tobacco). Such compounds may be undesirable for human consumption. In some cases, however, such compounds may be beneficial for animal and/or human consumption.

The term "environmental contaminant" refers to a compound in the environment that is not normally found in the environment, or that is generally found in significantly lower levels in an uncontaminated environment than in an environment that is considered to be contaminated with the compound. In some cases, the environmental contaminant may be a heavy metal. Or, the environmental contaminant may be another compound that has potentially harmful or non-beneficial effects when ingested by animals and/or humans.

As defined herein, media may comprise compositions which are suited for maintenance or growth of biological tissue. Media may comprise water, buffered solutions, agar, or a growth medium, such as, but not limited to, the media described in the examples herein. Generally, any composition which is biologically compatible with the plant of interest may be suitable for use as a media or part of a media.

Also as defined herein, mutagenesis comprises a process that results in a modification of a DNA sequence. The term "mutagenesis" refers to the use of a mutagenic agent to induce genetic mutations within a population of individuals. A population to be mutagenized can comprise plants, parts of plants, or seeds. For mutagenized populations, the dosage of the mutagenic chemical or radiation can be determined experimentally for each type of plant tissue such that a mutation frequency that is below a threshold level characterized by lethality or reproductive sterility is obtained. The number of M1 generation seeds or the size of M1 plant populations resulting from the mutagenic treatments can be estimated based upon the expected frequency of mutations.

The types of mutations that may be induced in a gene include, for example, point mutations, additions, deletions, insertions, duplications, transitions, transversions, and/or inversions. Mutagenesis may cause frameshifts, or crosslinking of nucleotides, as well as modification/substitution of bases such that binding of proteins to DNA (e.g. transcription factors) is altered. Or, mutations may cause other sequence based alterations-of structure or function. Also included are hybrids made from such mutants as well as interspecific and intraspecific crosses.

In addition to the methods described in detail herein, in some embodiments, mutagenesis may be induced by growing plant cells in tissue culture, which can result in the production of somaclonal variants. Alternatively, application of standard protoplast culture methodologies developed for production of hybrid plants using protoplast fusion is also useful for generating plants having variant gene expression. Accordingly, protoplasts may be generated from a first and a second plant having variant gene expression. Calli may be cultured from successful protoplast fusions and plants regenerated. Resulting progeny hybrid plants may be identified and selected for variant gene expression according to methods described herein and may be used in a breeding protocols described herein. Also included are methods comprising genetic engineering such as site-directed mutagenesis.

The plants included in the plants of the invention also include plants (and/or lines derived from such plants) which may be genetically engineered using DNA from a different species (e.g., non-tobacco DNA for a tobacco plant) at a locus distinct from the genes relating to uptake of environmental contaminant or other non-natural chemicals. For example, plants which are genetically engineered to be resistant to pesticides and which are also modified by mutagenesis of tobacco genomic DNA to exhibit reduced uptake of at least one environmental contaminant or other non-natural chemical are included in the present invention. In one embodiment, the plants of the present invention comprise plants having essentially the same antibiotic resistance profile as the unmodified plant parent line, such that the modified plants do not comprise a novel antibiotic resistance as compared to the unmodified parent line.

A mutagen is defined as a substance (or treatment) which can change (mutate) the DNA in a cell. Suitable mutagenic agents include, for example, chemical mutagens and ionizing radiation. Typical chemical mutagens include, but are not limited to, ethyl methanesulfonate (EMS), nitrous acid, 5-bromouracil, methyl-nitrosoguanidine, sodium azide, acridine orange, ethidium bromide and frameshift mutagens such as proflavin and the like. Mutations can also be generated by radiation, such as UV, X-rays, γ-rays, fast neutron irradiation, and the like. Mutagens also include genetic elements such as viral vectors, transponsons, and the like, which can facilitate the insertion of foreign DNA into the tobacco genome.

Generally, the first generation treated with a mutagen comprises the M0 (or $M_0$) generation. Subsequent generations are then described as M1 (or $M_1$) (i.e., one generation after the mutagenesis event), M2 (two generations after the mutagenesis event) and the like. Thus, as used herein, M0 refers to plant cells (and plants grown therefrom) exposed to a mutagenic agent, while M1 refers to seeds produced by self-pollinated M0 plants, and plants grown from such seeds. M2 is the progeny (seeds and plants) of self-pollinated M1 plants, M3 is the progeny of self-pollinated M2 plants, M4 is the progeny of self-pollinated M3 plants, M5 is the progeny of self-pollinated M4 plants, and so forth. Thus, the Mn+1 (or $M_{n+1}$) generation each the progeny of self-pollinated plants of the previous Mn (or $M_n$) generation.

As used herein, a "modified plant", or "modified tobacco plant" or "modified tobacco" includes plants, tobacco plants and tobacco that is genetically modified (i.e., mutated) so as to have a different genotype and phenotype than the unmodified plant (e.g., tobacco) from which the modified plant is derived.

As used herein, the "unmodified plant from which the modified plant is derived" refers to the parent plant line used to generate mutant (i.e., "modified") plant lines. As used herein, the M0 generation would be the unmodified plant from which the modified M1 plant is derived.

As defined herein, the physical appearance of an organism comprises its phenotype, whereas the genetic composition of an organism comprises its genotype. Heterozygotes are defined as genomes which have different alleles (i.e., DNA sequences) at a locus of interest. For example, a heterozygous mutation would be a plant having a mutated sequence at only one allele. Thus, heterozygotes have two distinct alleles for a gene, each of which can be passed to the next generation. Homozygotes are defined as organisms having identical alleles at one or more loci. Thus, homozygotes carry the same alleles (e.g. two mutations or two normal sequences) at a locus of interest and, therefore, identical alleles will be passed to all progeny.

Tobacco having Altered Environmental Contaminants

The present invention provides methods of making tobacco plants having significantly altered uptake and/or levels of at least one environmental contaminant or other non-natural chemicals. In certain embodiments, the invention comprises methods for producing a modified tobacco plant or a portion thereof comprising generating a tobacco plant comprising significantly altered uptake and/or altered levels of environmental contaminant or other non-natural chemicals as compared to an unmodified tobacco plant or a portion thereof from which the modified plant is derived.

In certain embodiments, the present invention provides methods of making tobacco plants or a portion thereof (or tobacco lines derived from such plants) having a decreased uptake and/or reduced levels of at least one environmental contaminant or other non-natural chemical as compared to an unmodified tobacco plant or portion thereof from which the modified plant is derived. In certain embodiments, the invention comprises tobacco plants and/or tobacco products made from plants of the invention that have a decreased uptake and/or reduced levels of at least one environmental contaminant or other non-natural chemical as compared to an unmodified tobacco plant or portion thereof from which the modified plant is derived.

In other embodiments, the present invention provides methods of making tobacco plants or a portion thereof having significantly increased uptake and/or increased levels of at least one environmental contaminant or other non-natural chemicals as compared to an unmodified tobacco plant or portion thereof from which the modified plant is derived. In certain embodiments, the invention comprises tobacco plants, or tobacco lines derived from such plants, or products made from such plants, having significantly increased uptake and/or increased levels of at least one environmental contaminant or other non-natural chemical as compared to an unmodified tobacco plant or portion thereof from which the modified plant is derived.

In certain embodiments of each of the methods, plants, plant lines, or tobacco products of the invention, the environmental contaminant or other non-natural chemical may comprise a heavy metal. The heavy metal having altered uptake and/or altered levels may be at least one of arsenic (As), cadmium (Cd), chromium (Cr), nickel (Ni), lead (Pb), selenium (Se), zinc (Zn), copper (Cu), mercury (Hg) or silver (Ag). For example, in certain embodiments of each of the methods, plants, plant lines, or tobacco products of the invention the heavy metal having altered uptake and/or levels is cadmium. Or, other heavy metals and/or other selected elements may be altered in each of the methods, plants, plant lines, or tobacco products of the invention.

The present invention may be embodied in a variety of ways.

Methods of Making Tobacco having Altered Environmental Contaminants

Embodiments of the present invention provide methods of making tobacco plants or a portion thereof having altered uptake and/or altered levels of at least one environmental contaminant or other non-natural chemical as compared to an unmodified tobacco plant or portion thereof from which the modified plant is derived. The alteration in uptake and/or levels may be a reduction in the uptake and/or levels of the environmental contaminant or other non-natural chemical. Or, the alteration in uptake and/or levels may be an increase in the uptake and/or levels of the environmental contaminant or other non-natural chemical.

In certain embodiments of each of the methods of making tobacco plants or a portion thereof having altered uptake and/or altered levels of at least one environmental contaminant or other non-natural chemical as compared to an unmodified tobacco plant or portion thereof from which the modified plant is derived, the environmental contaminant or other non-natural chemical may comprise a heavy metal. The heavy metal having altered uptake and/or altered levels may be at least one of arsenic (As), cadmium (Cd), chromium (Cr), nickel (Ni), lead (Pb), selenium (Se), zinc (Zn), copper (Cu), mercury (Hg) or silver (Ag). In an embodiment, the heavy metal having altered uptake and/or levels is cadmium. Or, other heavy metals and/or other selected elements may have altered uptake and/or levels.

In certain embodiments where alteration of uptake or levels of a heavy metal is desired, the selection agent is a heavy metal. The heavy metal may be the same heavy metal for which alteration in uptake and/or levels is desired. For example, in certain embodiments, where alteration of cadmium uptake is desired, the selection agent is cadmium Thus, in one embodiment, the present invention comprises a method for producing a modified plant or a portion thereof (or a line derived from the plant) comprising an altered phenotype of altered uptake and/or altered levels of at least one environmental contaminant or other non-natural chemical as compared to an unmodified tobacco plant or portion thereof from which the modified plant is derived. The method may comprise incubating at least one seed (i.e., a seed or seeds (seed(s)), for the plant of interest in a solution comprising a mutagen. The method may also comprise washing the at least one seed free of the mutagen. The method may additionally comprise germinating the at least one seed and growing M0 at least one seedling, i.e., a seedling or seedlings (seedling(s)). At this point, the method may comprise adding a selection agent to the seedling(s), wherein the selection agent selects for a chimeric M0 plant, wherein the M0 chimeric plant at least partially comprises the predetermined altered phenotype. The method may then comprise growing the M0 plant to generate M1 seed(s), wherein the M1 seed(s) comprise at least one mutagenized M1 seed comprising the predetermined altered phenotype, and germinating the at least one mutagenized M1 seed to select for at least one M1 plant comprising the predetermined altered phenotype. In certain embodiments, the method may further comprise growing the at least one M I plant to generate M2 seed(s) and germinating the M2 seeds to grow M2 plants, wherein at least one of the M2 plants is a homozygote for a mutation conferring the ability to grow in the presence of the selection agent (e.g., an altered phenotype and genotype). In certain embodiments, the method may comprise germinating the M1 and/or M2 and/or M3 and/or M4 plants and/or subsequent generations derived from the M0 plants in a medium comprising a selection agent. Also in certain embodiments, the second medium comprising at least one selection agent is added to M0 seedlings at certain developmental stages, as during a predetermined time period after germination.

For example, in certain embodiments, the method may comprise incubating at least one tobacco seed from an unmodified tobacco plant in a solution comprising a mutagen; washing the at least one seed free of the mutagen; germinating the at least one seed and growing at least one M0 tobacco seedlings in the presence of a selection agent to generate at least one M0 tobacco plant comprising M1 tobacco seeds, wherein the M1 tobacco seeds from the chimeric tobacco plant comprise at least one mutagenized M1 tobacco seed; and germinating the at least one mutagenized M1 tobacco seed to select for a modified M1 tobacco plant comprising significantly altered uptake and/or altered levels of environmental contaminant or other non-natural chemicals as compared to the unmodified tobacco plant.

In alternate embodiments, the modified plant (or a line derived from the plant) has at least a 10, 20, 30, 40, 50, 60, 70, 80, 90 or 100% decrease in at least one environmental contaminant or other non-natural chemical. In alternate embodiments, the modified plant has at least a 1.2, 1.5, 2, 4, 6, 8, 10, 20, 50 or 100-fold reduction in at least one environmental contaminant or other non-natural chemical. For example, in certain embodiments, the modified tobacco plant comprises at least a 100%, 90%, 80%, 70%, 60%, 50%, 40%, 30%, 20% or 10% reduction in cadmium levels.

In alternate embodiments, the modified plant (or a line derived from the plant) has at least a 10, 20, 30, 40, 50, 100, 200 or 500% increase in at least one environmental contaminant or other non-natural chemical. In alternate embodiments, the modified plant has at least a 1.2, 1.5, 2, 4, 6, 8, 10, 20, 50 or 100-fold increase in at least one environmental contaminant or other non-natural chemical. For example, in certain embodiments, the modified tobacco plant comprises at least a 10, 20, 30, 40, 50, 100, 200 or 500% increase in cadmium levels.

Also in certain embodiments of the methods of the invention, a medium comprising at least one selection agent is added to M0 seedlings at certain developmental stages, as during a predetermined time period after germination. For tobacco (e.g., *Nicotiana tabacum*) a medium comprising at least one selection agent may be added to M0 seedlings 7 to 14 days after germination. For example, the second medium comprising at least one selection agent may be added to M0 seedlings about 10 days after germination. In alternate embodiments, the selection may be continuously present during growth of the M0 seedlings.

As discussed further herein, a variety of plants may be modified using the methods of the invention. In certain embodiments, the plant comprises an alloploid genome. In certain embodiments, the plant is tobacco. In certain preferred embodiments, the tobacco is the genus *Nicotiana*. More preferably, the tobacco may comprise the species *Nicotiana tabacum*. Or, as described herein, any of the genus of *Nicotiana* thereof may be used. Such members are described in U.S. Patent Publication Nos. 2006/0185686 and 2011/0174323, the disclosures of which are incorporated by reference in their entireties herein.

Or, other tobaccos as described in more detail herein may be used. For example, tobaccos used in the methods of the invention may include wild tobaccos or tobaccos that have been genetically modified in some manner. Thus, the tobaccos may include types of tobaccos such as flue-cured tobacco, burley tobacco, sun-cured tobacco (e.g., Oriental tobacco or Indian Kurnool), Maryland tobacco, dark tobacco, dark-fired tobacco, dark air cured (e.g., passanda, cubano, jatim and bezuki tobaccos) or light air cured (e.g., North Wisconsin and galpao tobaccos), and Rustica tobaccos, as well as other rare or specialty tobaccos or even green or uncured tobaccos. Representative Oriental tobaccos include katerini, prelip, komotini, xanthi and yambol tobaccos.

In certain embodiments, the mutagen is ethyl methanesulfonate (EMS). In some embodiments, the EMS comprises a final concentration of 0.01 to 2%. Or, the EMS may comprise a final concentration of 0.05 to 1%. Or, the EMS may comprise a final concentration of 0.1 to 0.7%. For example, in certain embodiments a concentration of 0.5% may be used. Or, other chemical mutagens (or irradiation) may be used.

In certain embodiments, the mutagenized seeds are suspended within solidified agar plates containing the selection agent. In other embodiments, seeds may be suspended in a nutrient medium and applied to a semi-permeable surface for growth prior to addition of the selection agent. Or, selection may be performed using a hydroponic system or in soil. Or, other methods of in vitro selection known in the art may be used.

Embodiments of the present invention comprise methods for plant mutagenesis that includes a selection step at the M0 chimeric stage. For example, in embodiments of each of the methods, plants (plant lines) and products of the invention, the invention comprises selection of plants comprising resistance to high (e.g., potentially lethal) amounts of a heavy metal as a selection agent. The resistance may be due to an alteration in uptake and/or levels that comprises a reduction in the uptake and/or levels of the environmental contaminant or other non-natural chemical. Or, the resistance may be due to an alteration in uptake and/or levels that comprises an increase in the uptake and/or levels of the environmental contaminant or other non-natural chemical.

For example, in embodiments of each of the methods, plants (plant lines) and products of the invention, the invention comprises selection of plants comprising resistance to high (e.g., potentially lethal) amounts of cadmium (Cd) as a selection agent. Or, other selection agents, e.g., other heavy metal environmental contaminants or other non-natural chemicals, may be used.

The concentration of the selection agent may vary depending upon the nature of the environment and the selection agent used. In some embodiments, where cadmium is the selection agent, the cadmium is present at a concentration ranging from about 0.02 to about 15 mM, or 0.04 to about 10 mM, or about 0.050 to about 5 mM. Or, the cadmium may be present at a concentration ranging from about 0.075 to about 1 mM. Or, the cadmium is present at a concentration ranging from 0.1 to about 0.3 mM. Or, the cadmium selection agent may be present at about 0.15 mM.

The M0 plant will, in certain embodiments, comprise a subpopulation of cells resistant to the selection agent; these cells may confer viability to the entire plant when the plant is grown in the presence of a selection agent such as, but not limited to, elevated levels of cadmium. The present invention thus can eliminate the growth of a large population of the M0 plants for production of M1 seeds and thereby substantially reduces the number of progeny that must be screened at the M1 stage, thus resulting in a cost-effective plant breeding program suitable for large plants, or plants comprising complex genomes, such as tobacco. Other methods used to produce *N. tabacum* lines comprising a significantly increased amino acid content, and specifically, a significant increase in threonine are described in U.S. Pat. Nos. 6,730,832, 7,173, 170 and 7,825,305, the disclosures of which are incorporated by reference in their entireties herein.

Embodiments of the invention may also comprise seeds derived from modified plants that have been generated using the methods of the invention, wherein the seeds are capable of propagating the modified plant lines having altered uptake and/or altered levels of at least one environmental contaminant or other non-natural chemical as compared to an unmodified tobacco plant or portion thereof from which the modified plant is derived. The alteration in uptake and/or levels may be a reduction in the uptake and/or levels of the environmental contaminant or other non-natural chemical. Or, the alteration in uptake and/or levels may be an increase in the uptake and/or levels of the environmental contaminant or other non-natural chemical.

In certain embodiments of the seeds made by the methods of the invention, the environmental contaminant or other non-natural chemical may comprise a heavy metal. The heavy metal having an altered uptake and/or altered levels may be at least one of arsenic (As), cadmium (Cd), chromium (Cr), nickel (Ni), lead (Pb), selenium (Se), zinc (Zn), copper (Cu), mercury (Hg) or silver (Ag). In an embodiment, the heavy metal having altered uptake and/or levels is cadmium. Or, other heavy metals and/or other selected elements may be altered in seeds made by the method of the invention.

Also, as discussed in more detail herein, the invention comprises tobacco products derived from plants and/or plant lines generated using the methods of the invention such as leaves for chewing tobacco, flue-cured leaves for smoking tobacco, and other known tobacco products. In certain embodiments, the present invention comprises methods for altering the levels of at least one environmental contaminant or non-natural compound that may be present in the tobacco and/or generated upon heating the tobacco and/or improving the flavor of a tobacco product, comprising generating a modified tobacco plant having altered uptake and/or altered levels of at least one environmental contaminant or non-natural chemical (or a compound derived therefrom by heating the tobacco), mixing the modified tobacco with unmodified tobacco, and including the mixture in a tobacco product.

Preferably, the modified tobacco plant is made by mutagenizing tobacco seeds and selecting for at least partially mutagenized plants having altered uptake and/or altered levels of at least one environmental contaminant or other non-natural chemical as compared to an unmodified tobacco plant or portion thereof from which the modified plant is derived.

The alteration in uptake and/or levels may be a reduction in the uptake and/or levels of the environmental contaminant or other non-natural chemical. Or, the alteration in uptake and/or levels may be an increase in the uptake and/or levels of the environmental contaminant or other non-natural chemical Thus, embodiments the present invention relate to utilization of a method for producing plants with an altered phenotype by selection at the M0 chimeric stage and the use of this method to product plants having a decrease in at least one amino acid. Mutagenesis has been used as a conventional breeding method to develop improved cultivars of a number crops, including tobacco (see e.g. A. M. van Harten, *Mutation Breeding: Theory and Practical Applications*, pp. 1-63, Cambridge Univ. Press, New York, N.Y., 1998). Generally, the target plant materials used to develop desired mutant using chemical mutagens are classified into two categories: (1) seed and (2) tissue or cell culture.

For example, seeds may be treated with specific mutagens, and the surviving seeds grown to produce their progenies (e.g. Heremans and Jacobs, 1995). The generation that grows from the mutagenized seed is called the M0 generation, and the progeny collected from the M0 plants are the M1 generation, from which the desired mutants are usually selected. Further selection of plants which are homozygous for the mutation of interest may be made by growing progeny from M1 plants (i.e. the M2 generation) under selective conditions.

Although mutagenesis and selection can be performed on tissue culture cells (e.g. Cattoir-Reynaerts et al., 1983; Dotson et al., 1990; Hibberd et al., 1980), the mutant cells or tissues must be regenerated to fertile plants. Establishment of a system for regeneration of a fertile plant from the genotype of interest can be time-consuming, expensive, and requires a high level of technical expertise. In addition, undesired somaclonal variation often occurs in regenerated mutants of interest as a result of autosomal chromosome duplications.

Genetic engineering has also been used produce transgenic plants. It has been shown that expression of a bacterial heavy metal transporter in *Arabidopsis* can enhance resistance to and decrease uptake of heavy metals (J. Lee et al., *Plant Physiology*, 2003, 133:589-596). Still, this type of approach is technically demanding, requires introduction of foreign DNA into the genome, and generally does not generate the wide variety of mutants needed for propagation of a crop in various ecosystems. In addition, the effects of transgenic crops produced by genetic engineering on the long-term stability of ecosystems is not known (N. C. Ellstrand, 2001, *Plant Physiol.*, 125: 1543-1545). Finally, transgenic crops have not been widely accepted by the public, as for example, in certain European countries.

It is therefore an object of the present invention to utilize a screening method whereby the screening is at least in part performed using M0 plants. Referring now to FIG. 1, in one aspect, the invention provides a method of producing tobacco (e.g., *Nicotiana tabacum*) lines having an altered (i.e., increased or reduced) uptake and/or an altered amount of at least one environmental contaminant or other non-natural chemical. In an embodiment, the method comprises the steps of: (a) mutagenizing tobacco seeds 2 in a solution containing the mutagen ethyl methane-sulfonate (EMS) 4 at a concentration of about 0.5% for 20 hrs; (b) washing the mutagenized seeds in water 6; (c) sterilizing the seeds 2 with 70% ethanol followed by 20% Chlorox bleach 8 on an agitating shaker 10; (d) rinsing with sterile water 6; (e) suspending the seeds 2 in nutrient medium with 0.1% Agar (a semi-solid colloidal suspension) 12; (f) applying about 0.750 ml of the suspension with about 50 seeds 2 onto a solidified phytoagar plate containing a selection agent 16; (g) germinating the seeds and growing the seedlings 18 in a tissue culture room at 25° C. with a 16-h photoperiod from cool-white fluorescent lamps; (h) transplanting the healthy seedlings 18 to soil and growing as M0 plants 22 in a greenhouse; (i) planting individual M1 seeds 23 from M0 plants 22 in a field to generate M1 plants 24; (j) testing the M1 plants for altered levels of the environmental contaminant or other non-natural chemical of interest (e.g., Cd); (k) growing M2 seeds 25 from the M1 plants with an altered level of the environmental contaminant or other non-natural chemical of interest, and testing for M2 lines 26 producing altered levels of the environmental contaminant or other non-natural chemical of interest (e.g., Cd). These non-chimeric tobacco plants may be a mixture of heterozygotes and homozygotes. Additional selection step may be added for selection of tobacco lines in the field based on chemistry.

These modified plants and/or lines also provide the basis for the production of hybrid lines, utilizing as one or both parents, the novel lines of the present invention. Also within the scope of the present invention are clones, somaclones, and derivatives of the novel lines.

In certain embodiments, the methods of the present invention are used to generate a tobacco plant derived from one of the tobacco lines described herein. For example, in certain embodiments, the methods of the invention are used to generate a tobacco plant comprising at least one of the 10TN-278-2, 10TN-253-4, 10TN-256-1 or 10-TN-287-4 lines. Or, the invention may comprise methods to make other tobacco lines described herein. Thus, in certain embodiments, the modified tobacco plants made by the methods of the invention may comprise at least one of the 10TN-278-2, 10TN-253-4, 10TN-256-1 or 10-TN-287-4 lines described herein, wherein a representative sample of seeds for these lines have been deposited with the American Type Culture Collection (ATCC, 10801 University Blvd., Manassas, Va. 20110-2209), on Feb. 21, 2012, under conditions prescribed by the Budapest Treaty, and which will have all restrictions on accessibility of the seeds irrevocably removed upon issuance of a patent. The deposited seeds have been tested and designated as viable as of Mar. 20, 2012, and assigned ATCC Accession Numbers PTA-12602(10TN-278-2), PTA-12601 (10TN-253-4), PTA-12599 (10TN-256-1) and PTA-12600 (10TN-287-4), respectively.

Tobacco Plants having Altered Levels of at Least One Environmental Contaminant

In certain embodiments, the invention comprises plants or a portion thereof having significantly altered uptake and/or altered levels of at least one environmental contaminant or other non-natural chemical as compared to an unmodified tobacco plant or portion thereof from which the modified plant is derived. In certain embodiments, the invention comprises a modified tobacco plant or a portion thereof comprising a significantly altered uptake and/or altered levels of environmental contaminant or other non-natural chemicals as compared to an unmodified tobacco plant or a portion thereof from which the modified plant is derived, wherein the genome of the modified tobacco plant comprises a mutation that exhibits a dominant phenotype of resistance to growth in the presence of a selection agent.

The alteration in uptake and/or levels may be a reduction in the uptake and/or levels of the environmental contaminant or other non-natural chemical. Or, the alteration in uptake and/or levels may be an increase in the uptake and/or levels of the environmental contaminant or other non-natural chemical.

In certain embodiments of each of the plants of the invention, the environmental contaminant or other non-natural chemical may comprise a heavy metal. The heavy metal having altered uptake and/or altered levels may be at least one of arsenic (As), cadmium (Cd), chromium (Cr), nickel (Ni), lead (Pb), selenium (Se), zinc (Zn), copper (Cu). mercury (Hg) or silver (Ag). In an embodiment, the heavy metal having altered uptake and/or levels is cadmium. Or, other heavy metals and/or other selected elements may have altered uptake and/or levels in the plants of the invention.

In certain embodiments where alteration of uptake or levels of a heavy metal is desired, the selection agent is a heavy metal. The heavy metal may be the same heavy metal for which alteration in uptake and/or levels is desired. For example, in certain embodiments, where alteration of cadmium uptake is desired, the selection agent is cadmium.

As discussed further herein, a variety of plants may be modified. In certain embodiments, the plant comprises an alloploid genome. In certain embodiments, the plant is tobacco. In certain preferred embodiments, the tobacco is the genus *Nicotiana*. More preferably, the tobacco may comprise the species *Nicotiana tabacum*. Or, as described herein, any of the genus of *Nicotiana* may be used. Such tobaccos are described in U.S. Patent Publication Nos. 2006/0185686 and 2011/0174323, the disclosures of which are incorporated by reference in their entireties herein.

Or, other tobaccos may be used. For example, tobaccos used to generate the plants of the invention may include wild tobaccos or tobaccos that have been genetically modified in some manner. Thus, the tobaccos may include types of tobaccos such as flue-cured tobacco, burley tobacco, sun-cured tobacco (e.g., Oriental tobacco or Indian Kurnool), Maryland tobacco, dark tobacco, dark-fired tobacco, dark air cured (e.g., passanda, cubano, jatim and bezuki tobaccos) or light air cured (e.g., North Wisconsin and galpao tobaccos), and Rustica tobaccos, as well as other rare or specialty tobaccos or even green or uncured tobaccos. Representative Oriental tobaccos include katerini, prelip, komotini, xanthi and yambol tobaccos.

Thus, in certain embodiments, the present invention may comprise a tobacco plant or a portion thereof comprising a modified tobacco having significantly altered uptake and/or altered levels of at least one environmental contaminant or other non-natural chemical as compared to an unmodified tobacco plant or portion thereof from which the modified plant is derived. The alteration in uptake and/or levels may be a reduction in the uptake and/or levels of the environmental contaminant or other non-natural chemical. Or, the alteration in uptake and/or levels may be an increase in the uptake and/or levels of the environmental contaminant or other non-natural chemical.

For example, the present invention may comprise a tobacco plant or a portion thereof comprising a significantly altered uptake and/or altered levels of at least one environmental contaminant or other non-natural chemical as compared to an unmodified tobacco or a portion thereof wherein the genome of the modified tobacco plant comprises an alloploid genome having a mutation that exhibits a dominant phenotype of resistance to growth in the presence of cadmium or another selection agent.

The plants (e.g., tobacco plants) included in the present invention also include plants (and/or lines derived from such plants) which may be genetically engineered using foreign (e.g., non-tobacco) DNA at a locus distinct from the genes relating to levels of the environmental contaminant or other non-natural chemical of interest in the tobacco (e.g., genes relating to uptake of the environmental contaminant or other non-natural chemical of interest). For example, tobacco plants which are genetically engineered to be resistant to pesticides and which are also modified by mutagenesis of tobacco genomic DNA (e.g., at a gene relating to uptake of the environmental contaminant or other non-natural chemical of interest) to have a significantly altered uptake and/or altered levels of at least one environmental contaminant or other non-natural chemical as compared to an unmodified plant from which the modified plant is derived, are included in the present invention.

Also, embodiments of the present invention may comprise a modified tobacco plant or a portion thereof, or a tobacco line derived from the plant, having a significantly altered uptake and/or altered levels of at least one environmental contaminant or other non-natural chemical as compared to an unmodified parent tobacco plant or a portion thereof and/or tobacco line from which the modified plant is derived, wherein the genome of the modified tobacco plant consists of, or consists essentially of, plant DNA. Preferably, the genome of the modified tobacco plant consists of, or consists essentially of tobacco DNA.

The present invention also includes a modified tobacco plant or a portion thereof and/or a tobacco line derived from the plant having significantly altered uptake and/or altered levels of at least one environmental contaminant or other non-natural chemical as compared to an unmodified parent tobacco line or a portion thereof, wherein the modified plant has consists of, or consists essentially of, the same antibiotic resistance as the unmodified parent line.

In certain embodiments of each of the tobacco plants of the invention, the environmental contaminant or other non-natural chemical may comprise a heavy metal. The heavy metal having altered uptake and/or reduced levels may be at least one of arsenic (As), cadmium (Cd), chromium (Cr), nickel (Ni), lead (Pb), selenium (Se), zinc (Zn), copper (Cu), mercury (Hg) or silver (Ag). In an embodiment, the heavy metal having altered uptake and/or levels is cadmium. Or, other heavy metals and/or other selected elements may have altered uptake and/or levels.

Thus, in another aspect, the present invention comprises a modified tobacco plant or a portion thereof, or a tobacco line derived from the plant, having a significantly altered uptake and/or altered levels of at least one environmental contaminant or other non-natural chemical as compared to an unmodified parent tobacco plant, wherein the genome of the modified tobacco plant consists of, or consists essentially of, plant DNA, and/or wherein the modified tobacco plant is produced by the steps of mutagenesis of tobacco genomic DNA and selection of M0 plants having a mutation of interest. More preferably, the gene or genes of the modified tobacco plant relating to the uptake and/or levels of the environmental contaminant or other non-natural chemical of interest consist of, or consist essentially of tobacco genomic DNA. The alteration in uptake and/or levels may be a reduction in the uptake and/or levels of the environmental contaminant or other non-natural chemical. Or, the alteration in uptake and/or levels may be an increase in the uptake and/or levels of the environmental contaminant or other non-natural chemical.

Thus, in certain embodiments, the present invention comprises a modified tobacco plant and/or a tobacco line derived from the tobacco plant having a significantly altered uptake and/or altered levels of at least one environmental contaminant or other non-natural chemical as compared to an unmodified parent tobacco line, wherein the tobacco plant is produced by mutagenesis of tobacco genomic DNA and selection of M0 plants having a mutation of interest. The alteration in uptake and/or levels may be a reduction in the uptake and/or levels of the environmental contaminant or other non-natural chemical. Or, the alteration in uptake and/or levels may be an increase in the uptake and/or levels of the environmental contaminant or other non-natural chemical. In certain embodiments, the tobacco plant is produced by the steps of: mutagenizing at least a tobacco seed(s); germinating the mutagenized seed(s) in the presence of a selection agent e.g., cadmium and/or another heavy metal for production of tobacco having altered cadmium and/or other heavy metal uptake; growing at least one M0 plant in the presence of the selection agent to generate M1 seed(s), wherein the M1 seed(s) comprise at least one mutagenized M1 seed; and germinating the at least one mutagenized M1 seed in medium to select for a mutagenized M1 plants. Thus, in an embodiment, the modified tobacco plant is made by a method comprising the steps of: incubating at least one tobacco seed from an unmodified tobacco plant in a solution comprising a mutagen; washing the at least one seed free of the mutagen; germinating the at least one seed and growing at least one M0 tobacco seedlings in the presence of a selection agent to generate at least one M0 tobacco plant comprising M1 tobacco seeds, wherein the M1 tobacco seeds from the chimeric tobacco plant comprise at least one mutagenized M1 tobacco seed; and germinating the at least one mutagenized M1 tobacco seed to select for a modified M1 tobacco plant comprising significantly altered uptake and/or altered levels of environmental contaminant or other non-natural chemicals as compared to the unmodified tobacco plant. In certain embodiments, the method of preparing the modified plant includes the steps of growing the M1 tobacco plants to generate M2 seed(s), and further germinating the M2 seeds to grow M2 plants, wherein at least one of the M2 plants is a homozygote for a mutation conferring the ability to grow in the presence of increased a selection agent (e.g., cadmium). In certain embodiments, the method may comprise germinating the M1 and/or M2 and/or M3 and/or M4 plants and/or subsequent generations derived from the M0 plants in a medium (or soil) comprising a selection agent.

In alternate embodiments, the modified plant (or a line derived from the plant) has at least a 10, 20, 30, 40, 50, 60, 70, 80, 90 or 100% decrease in at least one environmental contaminant. In alternate embodiments, the modified plant has at least a 1.2, 1.5, 2, 4, 6, 8, 10, 20, 50 or 100-fold reduction in at least one environmental contaminant or other non-natural chemical. For example, in certain embodiments, the modified tobacco plant comprises at least a 100%, 90%, 80%, 70%, 60%, 50%, 40%, 30%, 20% or 10% reduction in cadmium levels.

In alternate embodiments, the modified plant (or a line derived from the plant) has at least a 10, 20, 30, 40, 50, 100, 200 or 500% increase in at least one environmental contaminant. In alternate embodiments, the modified plant has at least a 1.2, 1.5, 2, 4, 6, 8, 10, 20, 50 or 100-fold increase in at least one environmental contaminant or other non-natural chemical. For example, in certain embodiments, the modified tobacco plant comprises at least a 10, 20, 30, 40, 50, 100, 200 or 500% increase in cadmium levels.

Thus, in certain embodiments, the present invention provides tobacco plants and/or lines derived from such plants that have been mutated so as to exhibit altered levels (i.e., concentration) of at least one environmental contaminant or other non-natural chemical as compared to an unmodified tobacco plant or portion thereof from which the modified plant is derived.

In certain embodiments, these novel lines have less than 0.5 micrograms (µg) cadmium per gram of dry weight of tobacco in flue cured leaf. This may represent about a 2-fold decrease in cadmium over the unmodified *N. tabacum* parent, which may normally yields a maximum of about 0.9-1.25 µg cadmium per milligram of dry weight of tobacco depending upon the field, time of year and/or other factors.

In other embodiments, these novel lines may uptake increase amounts of cadmium so as to have about 1.49 or more micrograms (μg) cadmium per gram of dry weight of tobacco in cured leaf. This may represent about a 20% increase in cadmium over unmodified *N. tabacum* parent, which normally yields a maximum of about 0.9-1.25 μg cadmium per milligram of dry weight of tobacco. Such plants may be useful for reducing the amounts of cadmium in a field.

The absolute amount of a specific environmental contaminant or other non-natural chemical may be dependent on processing of the leaf, or the developmental stage of the plant.

In certain embodiments, the present invention comprises a tobacco plant derived from one of the tobacco lines described herein. For example, in certain embodiments, the invention may comprise a tobacco plant comprising at least one of the 10TN-278-2, 10TN-253-4, 10TN-256-1 or 10-TN-287-4 lines. Or, the invention may comprise other tobacco lines described herein. Thus, in certain embodiments, the modified tobacco plants made by the methods of the invention may comprise at least one of the 10TN-278-2, 10TN-253-4, 10TN-256-1 or 10-TN-287-4 lines described herein, wherein a representative sample of seeds for these lines have been deposited with the American Type Culture Collection (ATCC, 10801 University Blvd., Manassas, Va. 20110-2209), on Feb. 21, 2012, under conditions prescribed by the Budapest Treaty, and which will have all restrictions on accessibility of the seeds irrevocably removed upon issuance of a patent, The deposited seeds have been tested and designated as viable as of Mar. 20, 2012, and assigned ATCC Accession Numbers PTA-12602 (10TN-278-2), PTA-12601 (10TN-253-4), PTA-12599 (10TN-256-1) and PTA-12600 (10TN-287-4), respectively.

Tobacco Products

In certain embodiments, the invention comprises compositions and/or tobacco products made from tobacco plants or a portion thereof having significantly altered uptake and/or reduced levels of at least one environmental contaminant or other non-natural chemical as compared to an unmodified tobacco plant or portion thereof from which the modified plant is derived. In certain embodiments, the invention may comprise a tobacco product comprising a modified tobacco having significantly altered uptake and/or altered levels of environmental contaminant as compared to an unmodified tobacco from which the modified tobacco is derived.

For various embodiments of each of the products of the invention, the alteration in uptake and/or levels may be a reduction in the uptake and/or levels of the environmental contaminant or other non-natural chemical. Or, the alteration in uptake and/or levels may be an increase in the uptake and/or levels of the environmental contaminant or other non-natural chemical if such chemicals are beneficial for consumption.

In certain embodiments of the various compositions and/or tobacco products of the invention, the environmental contaminant or other non-natural chemical may comprise a heavy metal. The heavy metal having altered uptake and/or altered levels may be at least one of arsenic (As), cadmium (Cd), chromium (Cr), nickel (Ni), lead (Pb), selenium (Se), zinc (Zn), copper (Cu), mercury (Hg) or silver (Ag). In an embodiment, the heavy metal having altered uptake and/or levels is cadmium. Or, other heavy metals and/or other selected elements may have altered uptake and/or levels. For example, in certain embodiments, the tobacco products of the invention may comprise a tobacco product comprising a modified tobacco having reduced levels of cadmium as compared to an unmodified tobacco. Or, other heavy metals or another environmental contaminant or other non-natural chemical may be reduced.

In certain embodiments where alteration of uptake or levels of a heavy metal is desired, the selection agent is a heavy metal. The heavy metal may be the same heavy metal for which alteration in uptake and/or levels is desired. For example, in certain embodiments, where alteration of cadmium uptake is desired, the selection agent is cadmium.

Any of the modified plants described herein may be used in the compositions and/or products of the invention. For example, the present invention may comprise a composition and/or tobacco product comprising a modified tobacco having altered uptake and/or altered levels of at least one environmental contaminant or other non-natural chemical as compared to an unmodified tobacco plant or portion thereof from which the modified plant is derived, wherein the genome of the modified tobacco plant comprises an alloploid genome, and/or has been genetically engineered using foreign (e.g., non-tobacco) DNA at a locus distinct from the genes relating to levels of the environmental contaminant or other non-natural chemical of interest in the tobacco, and/or wherein the genome of the modified tobacco plant consists of, or consists essentially of, plant DNA, and/or wherein the modified plant has consists of, or consists essentially of, the same antibiotic resistance as the unmodified parent line, and having a mutation that exhibits a dominant phenotype of resistance to growth in the presence of a selection agent (e.g., cadmium or another selection agent). The alteration in uptake and/or levels may be a reduction in the uptake and/or levels of the environmental contaminant or other non-natural chemical. Or, the alteration in uptake and/or levels may be an increase in the uptake and/or levels of the environmental contaminant or other non-natural chemical.

In alternate embodiments, the composition and/or tobacco product has at least a 10, 20, 30, 40, 50, 60, 70, 80, 90 or 100% decreased uptake and/or reduced levels of at least one environmental contaminant or other non-natural chemical as compared to non-modified tobacco. In alternate embodiments, the composition and/or tobacco product has at least a 1.2, 1.5, 2, 4, 6, 8, 10, 20, 50 or 100-fold decreased uptake and/or reduced levels of at least one environmental contaminant or other non-natural chemical. For example, in certain embodiments, the modified tobacco plant comprises at least a 100%, 90%, 80%, 70%, 60%, 50%, 40%, 30%, 20% or 10% reduction in cadmium levels.

In alternate embodiments, the composition and/or tobacco product has at least a 10, 20, 30, 40, 50, 100, 200 or 500% increased uptake and/or increased levels of at least one environmental contaminant or other non-natural chemical as compared to non-modified tobacco. In alternate embodiments, the composition and/or tobacco product has at least a 1.2, 1.5, 2, 4, 6, 8, 10, 20, 50 or 100-fold increased uptake and/or increased levels of at least one environmental contaminant or other non-natural chemical. For example, in certain embodiments, the modified tobacco plant comprises at least a 10, 20, 30, 40, 50, 100, 200 or 500% increase in cadmium levels.

As discussed further herein, a variety of tobacco plants may be modified to generate the compositions and/or products of the invention. In certain embodiments, the plant comprises an alloploid genome. In certain embodiments, the plant is tobacco. In certain preferred embodiments, the tobacco is the genus *Nicotiana*. More preferably, the tobacco may comprise the species *Nicotiana tabacum*. Or, as described herein, any of the genus of *Nicotiana* or blends thereof may be used. Such tobaccos and blends are described in U.S. Patent Publication Nos. 2006/0185686 and 2011/0174323, the disclosures of which are incorporated by reference in their entireties herein.

Or, other tobaccos and blends may be used. Tobaccos used in the products of the invention may vary and generally include wild tobaccos or tobaccos that have been genetically modified in some manner. For example, the tobaccos may include types of tobaccos such as flue-cured tobacco, burley tobacco, sun-cured tobacco (e.g., Oriental tobacco or Indian Kurnool), Maryland tobacco, dark tobacco, dark-fired tobacco, dark air cured (e.g., passanda, cubano, jatim and bezuki tobaccos) or light air cured (e.g., North Wisconsin and galpao tobaccos), and Rustica tobaccos, as well as other rare or specialty tobaccos or even green or uncured tobaccos. Representative Oriental tobaccos include katerini, prelip, komotini, xanthi and yambol tobaccos.

In certain embodiments of the invention, different parts of the plant and/or individual tobacco grades may be evaluated for the level of an environmental contaminant or other non-natural chemical and/or other non-natural chemicals in smoke. For example, in certain embodiments, upper stalk grades may have less cadmium (or other non-natural contaminants or environmental contaminants) than lower stalk grades. Also, certain tobacco-specific grades (e.g., burley and oriental grades) may have reduced or increased levels of cadmium (or other non-natural contaminants or environmental contaminants) as compared to other grades (e.g., flue-cured grades).

In certain embodiments, the invention provides a heat-treated tobacco composition. As used herein, the term "heat-treated tobacco composition" refers to a composition comprising a tobacco material that has been thermally processed at an elevated temperature, such as a temperature of at least about 60° C., more typically at least about 100° C., for a time sufficient to alter the character or nature of the tobacco composition, for example, for as at least about 10 minutes. In some cases, the heat treatment process may alter the chemistry or sensory characteristics (e.g., taste and aroma) of the tobacco composition. The heat treatment process can be a modified version of conventional tobacco treatment processes, such as processes adapted to form flavorful and aromatic compounds (e.g., Maillard reaction products), processes adapted for pasteurization of tobacco compositions, processes for preparing tobacco casing products, reconstituted tobacco processes (e.g., cast sheet and paper-making reconstituted tobacco processes), tobacco extraction processes, reordering processes, toasting processes, steam treatments, and drying processes.

Examples of tobacco products that may be generated using the tobacco plants and/or tobacco lines of the present invention are described in U.S. Patent Publication No. US 2011/0048434, the disclosure of which is incorporated by reference in its entirety herein. Thus, the tobacco compositions of the invention can be used as an additive for a smoking article, or as a smokeless tobacco composition, such as loose moist snuff, loose dry snuff, chewing tobacco, pelletized tobacco pieces, tobacco comprising an insulated fuel element as described in U.S. Pat. No. 5,819,751 (i.e., heat not burn technology), extruded or formed tobacco strips, pieces, rods, or sticks, finely divided ground powders, finely divided or milled agglomerates of powdered pieces and components, flake-like pieces, molded processed tobacco pieces, pieces of tobacco-containing gum, rolls of tape-like films, readily water-dissolvable or water-dispersible films or strips, or capsule-like materials.

Tobaccos used in the invention, including tobacco compositions intended to be used in a smokeless form as tobacco products of the invention, may incorporate a single type of tobacco (e.g., in a so-called "straight grade" form). For example, the tobacco within a tobacco composition may be composed solely of flue-cured tobacco (e.g., all of the tobacco may be composed, or derived from, either flue-cured tobacco lamina or a mixture of flue-cured tobacco lamina and flue-cured tobacco stem). The tobacco within a tobacco composition also may have a so-called "blended" form. For example, the tobacco within a tobacco composition of the present invention may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other exemplary tobacco blends may incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis or similar percentages (e.g., within about a 10% range of each of the individual components for a total of 100%). Other exemplary tobacco blends incorporate about 20 to about 30 parts Oriental tobacco and about 70 to about 80 parts flue-cured tobacco (e.g., within about a 10% range of each of the individual components for a total of 100%). Or, other tobaccos or tobacco blends, such as those described in U.S. Patent Publication No. 2006/0185686 the disclosure of which is incorporated by reference in its entirety herein may be used. Or, other blends may be used.

The relative amount of tobacco within the composition and/or tobacco product may vary. Preferably, the amount of tobacco within the tobacco product ranges from at least about 10 percent or at least about 25 percent, on a dry weight basis. In certain instances, the amounts of other components within the tobacco product may exceed about 20, 30, 40, 50, 60, 70, 80 or 90 percent, on a dry weight basis. A typical range of tobacco material in the tobacco product may range from about 10 to about 60 weight percent, more often about 20 to about 40 weight percent on a dry basis. For example, the tobacco product may include additional flavorants, fillers, binders, buffering agents, colorants, and humectants.

The tobacco products of the invention may be formulated as various articles of manufacture. For smokeless tobacco compositions, the tobacco compositions of the invention can be formed into desired product shapes. The method and apparatus used to form the tobacco composition will depend on the desired shape. For example, the tobacco composition can have the form of compressed tobacco pellets, multi-layered extruded pieces, extruded or formed rods or sticks, compositions having one type of tobacco formulation surrounded by a different type of tobacco formulation, rolls of tape-like films, readily water-dissolvable or water-dispersible films or strips, or capsule-like materials possessing an outer shell (e.g., a pliable or hard outer shell that can be clear, colorless, translucent or highly colored in nature) and an inner region possessing tobacco or tobacco flavor.

The tobacco compositions of the invention may be useful as additives for the manufacture of smoking articles. The tobacco of the invention can be incorporated into the tobacco blends, representative cigarette components, and representative cigarettes manufactured therefrom. For example, the tobacco leaves of the present invention can be incorporated into a smoking article as part of the smokeable material charge. Or, the tobacco of the invention can be incorporated into a cigarette filter (e.g., in the filter plug, plug wrap, or tipping paper) or incorporated into cigarette wrapping paper, preferably on the inside surface, during the cigarette manufacturing process.

In certain embodiments of the compositions and/or tobacco products of the invention, the resulting smoking article is characterized by a significantly altered levels of at least one environmental contaminant or non-natural chemical, or a compound derived therefrom, in mainstream smoke during use. For example, the smoking article can be characterized by a significantly decreased level of at least one environmental contaminant or other non-natural chemical, or a compound derived therefrom, in mainstream smoke relative to an control smoking article (i.e., a comparable smoking article except containing unmodified tobacco in place of the modified tobacco of the invention) of at least about 10 percent, at least about 20 percent, at least about 30 percent, at least about 40 percent, at least about 50 percent, at least about 60 percent, at least about 70 percent, at least about 80 percent, or more. The smoking article of the invention, such as a cigarette, containing the tobacco composition of the invention can produce a significantly decreased level of at least one environmental contaminant or other non-natural chemical, or a compound derived therefrom, by weight in mainstream smoke as compared to a control smoking article smoked using the same smoking machine and under the same smoking conditions, such as the smoking machines and smoking conditions set forth in ISO 3308:1991 and ISO 4387:1991, which are incorporated by reference herein. Or, in some cases there may be an increase in a non-natural compound, or a compound derived therefrom, if such chemicals are beneficial for consumption.

In certain embodiments, these novel lines have less than 0.5 micrograms (μg) cadmium per gram of dry weight of tobacco in cured leaf. This may represent about a 2-fold decrease in cadmium over unmodified *N. tabacum* parent, which normally yields a maximum of about 0.33-2.24 μg/mg (see e.g., Lugon-Moulin et al., *Chemosphere*, 2006, 1074-1086), or about 0.9-1.25 μg cadmium per milligram of dry weight of tobacco. In some cases (e.g., where sludge has been applied to a field, the level of cadmium may be as high as 9.46 μg/mg (Adamu et al., *Environmental Pollution*, 1989, 56:113-126). The absolute amount of a specific environmental contaminant or other non-natural chemical may be dependent on the field, the time of year, processing of the leaf, or the developmental stage of the plant, as well as other factors.

In certain embodiments, the present invention comprises a composition (e.g., a tobacco product) comprising tobacco derived from one of the tobacco lines described herein. For example, in certain embodiments, the invention may comprise a composition comprising at least one of the 10TN-278-2, 10TN-253-4, 10TN-256-1 or 10-TN-287-4 lines. Or, the composition may comprise other tobacco lines described herein. Thus, in certain embodiments, the composition and/or tobacco product comprises may comprise at least one of the 10TN-278-2, 10TN-253-4, 10TN-256-1 or 10-TN-287-4 lines described herein, wherein a representative sample of seeds for these lines have been deposited with the American Type Culture Collection (ATCC, 10801 University Blvd., Manassas, Va. 20110-2209), on Feb. 21, 2012, under conditions prescribed by the Budapest Treaty, and which will have all restrictions on accessibility of the seeds irrevocably removed upon issuance of a patent. The deposited seeds have been tested and designated as viable as of Mar. 20, 2012, and assigned ATCC Accession Numbers PTA-12602 (10TN-278-2), PTA-12601 (10TN-253-4), PTA-12599 (10TN-256-1) and PTA-12600 (10TN-278-4), respectively.

The present invention may be better understood by reference to the following non-limiting examples.

EXAMPLE 1

Mutation of Tobacco

Seed from NL Madole, a dark-fired tobacco variety, and K326, a flue-cured variety, were mutagenized with 0.5% EMS (ethyl methane sulfonate) and designated as M0. The M0 mutant populations were screened on tissue culture media containing 150 μM Cd.

To generate mutagenized tobacco, various (i.e., about 10 separate) aliquots of the NL Madole or K326 seeds were incubated in a solution containing ethyl methane sulfonate (EMS) at a concentration of about 0.5% for 20 hrs. Both K326 seeds and non-mutagenized NL Madole seeds were used as the control. The treated seeds were then washed with MiliQ water (purified with an NANO pure II system; Barnstead/Thermolyne Corp.; Dubuque, Iowa) for 30 minutes and sterilized with 70% ethanol for 30 seconds followed by 20% Clorox for 20 min on an agitating shaker.

The M0 mutant populations were then screened on tissue culture media containing 150 μM Cd. Thus, after rinsing with sterile MiliQ water at least 5 times, the seeds (about 50 seeds per plate) were suspended in solidified phytoagar plates with ½ Murashige and Skoog Salt (MSS) medium+1.5% sucrose, 5 g phytoagar and selection agent (150 μM Cd). MSS medium is described in Table 1 of U.S. Pat. No. 7,173,170; the description of this medium is incorporated by reference herein in its entirety. The seeds were allowed to germinate in a tissue culture room at 25° C. with a 16-h photoperiod using cool-white fluorescent lamps (Sylvania, Danvers, Mass.) with an intensity of approximately 80 μE m$^{-2}$ s$^{-1}$. After 10 days, the growth medium was removed and the same medium containing 150 μM Cd, was added to the seedlings. The surviving plants were then transplanted into soil and grown in a greenhouse for development of *N. tabacum* lines resistant to high levels of Cd.

Surviving M0 plantlets selected on Cd-rich media were rescued and transferred to soil in a growth room. Later, these M0 plants were transferred to the greenhouse and self-seed was collected from each plant and designated as M1. M1 lines were grown under normal field conditions. Each M1 line was flue-cured according to traditional practices.

This M1 seed was rescreened by growing in the presence of the selection agent (i.e., 150 μM Cd) using a tissue culture vertical plate technique whereby plantlets were grown vertically and shoots and roots were measured. Selections were based on fresh shoot weight and root length. Analysis of shoot and root data revealed significant differences among the M1 lines tested. Selected M1 plants were transferred to the greenhouse and self seed was collected (M2) for further propagation.

EXAMPLE 2

Analysis of for Cd Levels in Various Tobacco Lines Mutated Using the Methods of the Invention Twenty-two potential fields were evaluated and soil samples were submitted for Cd analysis. A field containing relatively high levels of Cd was identified in Greeneville, Tenn. (see Table 1). M1 and M2 tobacco breeding lines were evaluated and screened under field conditions at this location.

In addition, several wild species of *N. tabacum* that have been reported to have resistance to Cd uptake were tested alongside M1 and M2 selections for comparison.

All samples were collected at bud stage. Lower leaf lamina was collected from individual M1 plants for analysis because of individual plant variation at the M1 generation. Lower leaf lamina was collected from whole plots of a few of the M2 lines for analysis. All lamina was frozen on dry ice, and freeze-dried to maintain leaf integrity. Freeze-dried samples were analyzed for content of Cd and other selected heavy metals. Table 1 below shows an analysis of acid (1N $HNO_3$) extracts of soil from the selected field for As, Cd, Cr, Ni, Pb and Se. Reported results are the average and standard deviation of duplicate 1 N HNO3 extracts corrected to the soil dry weight.

TABLE 1

| Metal | Conc. (µg/g) | Std. Dev. |
|---|---|---|
| As | 0.117 | 0.008 |
| Cd | 0.111 | 0.000 |
| Cr | 2.700 | 0.200 |
| Ni | 1.540 | 0.040 |
| Pb | 7.800 | 0.100 |
| Se | 0.020 | 0.008 |

Four plants from the M1 lines were selected for generation advancement to M2, bagged to prevent outcrossing and treated with TRACER® or BELT® insecticide to prevent seed damage by insects. A single plant was selected in each, and M2 line and M3 seed was produced as stated previously for the $M_1$ advancement. This field experiment was a randomized complete block design with three replicates. Data was analyzed using JMP® statistical software ($\alpha=0.05$) (SAS, Cary, N.C.).

Flue-cured Results: Results for M1 lines are shown in Table 2.

Ninety-six experimental flue-cured M1 selections were evaluated against K326 as the control (Table 2). It was found that twenty-four M1 selections accumulated significantly more Cd than control, and fifty lines accumulated significantly less Cd than control. Table 2 shows mean Cd content in individual flue-cured M1 breeding line selections. In Table 2, values for the control are shown in italics. Levels not connected by the same letter or symbol are significantly different. Two M1 selections, 10TN-269-2 and 10TN-266-2, shown in bold font in Table 2, accumulated less Cd than the GOTHI-ATEK® standard of 0.5µµg/g.

TABLE 2

| Entry | Pedigree/Name | Mean Cd (µg/g) |
|---|---|---|
| 10TN-290-1 | EMS K326 ($M_1$) | 1.488 A |
| 10TN-288-4 | EMS K326 ($M_1$) | 1.456 AB |
| 10TN-288-1 | EMS K326 ($M_1$) | 1.452 AB |
| 10TN-281-1 | EMS K326 ($M_1$) | 1.414 AB |
| 101-N-291-1 | EMS K326 ($M_1$) | 1.398 BC |
| 10TN-292-1 | EMS K326 ($M_1$) | 1.359 C |
| 10TN-277-3 | EMS K326 ($M_1$) | 1.341 C |
| 10TN-290-2 | EMS K326 ($M_1$) | 1.256 D |
| 10TN-293-2 | EMS K326 ($M_1$) | 1.179 E |
| 10TN-290-3 | EMS K326 ($M_1$) | 1.167 EF |
| 10TN-286-1 | EMS K326 ($M_1$) | 1.163 EF |
| 10TN-266-3 | EMS K326 ($M_1$) | 1.155 EF |
| 10TN-282-4 | EMS K326 ($M_1$) | 1.145 EF |
| 10TN-292-4 | EMS K326 ($M_1$) | 1.130 EF |
| 10TN-282-1 | EMS K326 ($M_1$) | 1.115 EF |
| 10TN-291-4 | EMS K326 ($M_1$) | 1.109 EFG |
| 10TN-291-2 | EMS K326 ($M_1$) | 1.096 FG |

TABLE 2-continued

| Entry | Pedigree/Name | Mean Cd (µg/g) |
|---|---|---|
| 10TN-290-4 | EMS K326 ($M_1$) | 1.036 GHI |
| 10TN-293-1 | EMS K326 ($M_1$) | 1.030 HI |
| 10TN-277-1 | EMS K326 ($M_1$) | 1.020 IJK |
| 10TN-282-3 | EMS K326 ($M_1$) | 1.009 IJKL |
| 10TN-280-1 | EMS K326 ($M_1$) | 1.004 IJKLM |
| 10TN-277-2 | EMS K326 ($M_1$) | 1.004 IJKLM |
| 10TN-281-3 | EMS K326 ($M_1$) | 0.999 IJKLMN |
| 10TN-286-4 | EMS K326 ($M_1$) | 0.984 IJKLMNO |
| 10TN-294-2 | EMS K326 ($M_1$) | 0.969 IJKLMNOP |
| 10TN-267-1 | EMS K326 ($M_1$) | 0.957 JKLMNOPQ |
| 10TN-274-3 | EMS K326 ($M_1$) | 0.956 JKLMNOPQ |
| 10TN-286-2 | EMS K326 ($M_1$) | 0.952 KLMNOPQR |
| 10TN-274-1 | EMS K326 ($M_1$) | 0.947 KLMNOPQRS |
| 10TN-281-2 | EMS K326 ($M_1$) | 0.939 LMNOPQRST |
| *10TN-2* | *K326 Control* | *0.938 OPQR* |
| 10TN-274-2 | EMS K326 ($M_1$) | 0.935 MNOPQRSTU |
| 10TN-283-2 | EMS K326 ($M_1$) | 0.935 MNOPQRSTU |
| 10TN-280-2 | EMS K326 ($M_1$) | 0.935 MNOPQRSTU |
| 10TN-266-1 | EMS K326 ($M_1$) | 0.935 MNOPQRSTU |
| 10TN-288-2 | EMS K326 ($M_1$) | 0.934 MNOPQRSTU |
| 10TN-280-3 | EMS K326 ($M_1$) | 0.928 NOPQRSTUV |
| 10TN-295-2 | EMS K326 ($M_1$) | 0.913 OPQRSTUVW |
| 10TN-292-2 | EMS K326 ($M_1$) | 0.913 OPQRSTUVW |
| 10TN-295-4 | EMS K326 ($M_1$) | 0.913 OPQRSTUVW |
| 10TN-291-3 | EMS K326 ($M_1$) | 0.912 OPQRSTUVW |
| 10TN-267-2 | EMS K326 ($M_1$) | 0.899 QRSTUVW |
| 10TN-287-1 | EMS K326 ($M_1$) | 0.892 QRSTUVWX |
| 10TN-295-3 | EMS K326 ($M_1$) | 0.889 QRSTUVWXY |
| 10TN-281-4 | EMS K326 ($M_1$) | 0.888 QRSTUVWXYZ |
| 1oTN-279-1 | EMS K326 ($M_1$) | 0.880 RSTUVWXYZ[ |
| 10TN-292-3 | EMS K326 ($M_1$) | 0.877 STUVWXYZ[ |
| 10TN-283-4 | EMS K326 ($M_1$) | 0.868 TUVWXYZ[ |
| 10TN-266-4 | EMS K326 ($M_1$) | 0.865 UVWXYZ[\ |
| 10TN-273-2 | EMS K326 ($M_1$) | 0.862 UVWXYZ[\ |
| 10TN-294-3 | EMS K326 ($M_1$) | 0.857 VWXYZ[\] |
| 10TN-294-4 | EMS K326 ($M_1$) | 0.852 WXYZ[\] |
| 10TN-288-3 | EMS K326 ($M_1$) | 0.849 WXYZ[\] |
| 10TN-274-4 | EMS K326 ($M_1$) | 0.844 WXYZ[\] |
| 10TN-279-3 | EMS K326 ($M_1$) | 0.842 WXYZ[\] |
| 10TN-269-1 | EMS K326 ($M_1$) | 0.841 WXYZ[\] |
| 10TN-282-2 | EMS K326 ($M_1$) | 0.837 XYZ[\] ' |
| 10TN-280-4 | EMS K326 ($M_1$) | 0.837 XYZ[\] 'a |
| 10TN-273-3 | EMS K326 ($M_1$) | 0.816 YZ[\] 'b |
| 10TN-293-3 | EMS K326 ($M_1$) | 0.816 Z[\] 'ab |
| 10TN-279-4 | EMS K326 ($M_1$) | 0.813 [\] 'abc |
| 10TN-275-3 | EMS K326 ($M_1$) | 0.794 \] 'abcd |
| 10TN-287-2 | EMS K326 ($M_1$) | 0.793 \] 'abcd |
| 10TN-267-4 | EMS K326 ($M_1$) | 0.785 ] 'abcde |
| 10TN-275-1 | EMS K326 ($M_1$) | 0.784 ] 'abcdef |
| 10TN-278-1 | EMS K326 ($M_1$) | 0.780 'abcdef |
| 10TN-295-1 | E0MS K326 ($M_1$) | 0.770 'abcdefg |
| 10TN-284-1 | EMS K326 ($M_1$) | 0.767 'abcdefgh |
| 10TN-277-4 | EMS K326 ($M_1$) | 0.763 abcdefghi |
| 10TN-283-3 | EMS K326 ($M_1$) | 0.761 bcdefghi |
| 1oTN-273-1 | EMS K326 ($M_1$) | 0.740 cdefghij |
| 10TN-294-1 | EMS K326 ($M_1$) | 0.738 defghij |
| 10TN-286-3 | EMS K326 ($M_1$) | 0.736 defghij |
| 10TN-285-1 | EMS K326 ($M_1$) | 0.734 defghij |
| 10TN-283-1 | EMS K326 ($M_1$) | 0.723 defghijk |
| 10TN-267-3 | EMS K326 ($M_1$) | 0.716 efghijk |
| 10TN-271-2 | EMS K326 ($M_1$) | 0.711 fghijkl |
| 10TN-279-2 | EMS K326 ($M_1$) | 0.705 ghijklm |
| 10TN-287-4 | EMS K326 ($M_1$) | 0.694 hijldmn |
| 10TN-269-4 | EMS K326 ($M_1$) | 0.691 ijldmn |
| 10TN-278-3 | EMS K326 ($M_1$) | 0.680 jklinno |
| 10TN-287-3 | EMS K326 ($M_1$) | 0.657 klinnop |
| 10TN-285-2 | EMS K326 ($M_1$) | 0.650 klinnop |
| 10TN-278-2 | EMS K326 ($M_1$) | 0.640 lrrmop |
| 10TN-289-4 | EMS K326 ($M_1$) | 0.635 mnop |
| 10TN-289-2 | EMS K326 ($M_1$) | 0.622 nopq |
| 10TN-273-4 | EMS K326 ($M_1$) | 0.614 opq |
| 1oTN-271-1 | EMS K326 ($M_1$) | 0.591 pqr |
| 10TN-269-2 | EMS K326 ($M_1$) | 0.590 pq |
| 10TN-275-2 | EMS K326 ($M_1$) | 0.590 pq |
| 10TN-278-4 | EMS K326 ($M_1$) | 0.588 pq |
| 10TN-275-4 | EMS K326 ($M_1$) | 0.551 qrs |
| 10TN-289-3 | EMS K326 ($M_1$) | 0.514 rs |
| 10TN-289-1 | EMS K326 ($M_1$) | 0.511 rst |

TABLE 2-continued

| Entry | Pedigree/Name | Mean Cd (µg/g) |
|---|---|---|
| 10TN-269-3 | EMS K326 ($M_1$) | 0.495 st |
| 10TN-266-2 | EMS K326 ($M_1$) | 0.444 t |

Dark Air-Cured Results:

Forty-nine experimental dark air-cured M2 lines were evaluated against NL Madole as the control (Table 3). Thus, Table 3 shows mean Cd content in dark air-cured M2 breeding lines. For Table 3, values for the control are shown in italics. Levels not connected by the same letter or symbol are significantly different. One line, 10TN-232, accumulated significantly more Cd than NL Madole. Several of the lines (in bold) accumulated much less Cd than NL Madole control (shown in italics).

TABLE 3

| Entry | Pedigree/Name | Mean Cd (µg/g) |
|---|---|---|
| 10TN-232 | EMS NL Madole ($M_2$) | 2.074 A |
| 10TN-227 | EMS NL Madole ($M_2$) | 1.660 AB |
| 10TN-226 | EMS NL Madole ($M_2$) | 1.591 ABC |
| 10TN-219 | EMS NL Madole ($M_2$) | 1.590 ABC |
| 10TN-237 | EMS NL Madole ($M_2$) | 1.535 ABC |
| 10TN-230 | EMS NL Madole ($M_2$) | 1.485 ABCD |
| 10TN-222 | EMS NL Madole ($M_2$) | 1.455 BCD |
| 10TN-235 | EMS NL Madole ($M_2$) | 1.398 BCD |
| 10TN-236 | EMS NL Madole ($M_2$) | 1.369 BCDE |
| 10TN-204 | EMS NL Madole ($M_2$) | 1.347 BCDEFG |
| 10TN-244 | EMS NL Madole ($M_2$) | 1.328 BCDEF |
| 10TN-208 | EMS NL Madole ($M_2$) | 1.324 BCDEFG |
| 10TN-225 | EMS NL Madole ($M_2$) | 1.301 BCDEFG |
| 10TN-214 | EMS NL Madole ($M_2$) | 1.286 BCDEFG |
| 10TN-248 | EMS NL Madole ($M_2$) | 1.263 BCDEFG |
| 10TN-209 | EMS NL Madole ($M_2$) | 1.261 BCDEFG |
| 10TN-238 | EMS NL Madole ($M_2$) | 1.261 BCDEFG |
| *10TN-200* | *NL Madole Control* | *1.251 BCDEFG* |
| 10TN-206 | EMS NL Madole ($M_2$) | 1.237 BCDEFG |
| 10TN-241 | EMS NL Madole ($M_2$) | 1.234 BCDEFG |
| 10TN-249 | EMS NL Madole ($M_2$) | 1.218 BCDEFG |
| 10TN-229 | EMS NL Madole ($M_2$) | 1.196 BCDEFG |
| 10TN-223 | EMS NL Madole ($M_2$) | 1.193 BCDEFG |
| 10TN-215 | EMS NL Madole ($M_2$) | 1.164 BCDEFG |
| 10TN-207 | EMS NL Madole ($M_2$) | 1.164 BCDEFG |
| 10TN-216 | EMS NL Madole ($M_2$) | 1.160 BCDEFG |
| 10TN-202 | EMS NL Madole ($M_2$) | 1.150 BCDEFG |
| 10TN-234 | EMS NL Madole ($M_2$) | 1.148 BCDEFG |
| 10TN-212 | EMS NL Madole ($M_2$) | 1.146 BCDEFG |
| 10TN-213 | EMS NL Madole ($M_2$) | 1.120 BCDEFG |
| 10TN-210 | EMS NL Madole ($M_2$) | 1.110 BCDEFG |
| 10TN-243 | EMS NL Madole ($M_2$) | 1.091 BCDEFG |
| 10TN-246 | EMS NL Madole ($M_2$) | 1.074 BCDEFG |
| 10TN-240 | EMS NL Madole ($M_2$) | 1.071 CDEFG |
| 10TN-247 | EMS NL Madole ($M_2$) | 1.059 CDEFG |
| 10TN-220 | EMS NL Madole ($M_2$) | 1.057 BCDEFG |
| 10TN-211 | EMS NL Madole ($M_2$) | 1.044 BCDEFG |
| 10TN-242 | EMS NL Madole ($M_2$) | 1.037 BCDEFG |
| 10TN-245 | EMS NL Madole ($M_2$) | 1.034 CDEFG |
| 10TN-250 | EMS NL Madole ($M_2$) | 0.992 DEFG |
| 10TN-217 | EMS NL Madole ($M_2$) | 0.983 DEFG |
| 10TN-221 | EMS NL Madole ($M_2$) | 0.959 DEFG |
| 10TN-203 | EMS NL Madole ($M_2$) | 0.956 CDEFG |
| 10TN-233 | EMS NL Madole ($M_2$) | 0.919 DEFG |
| 10TN-239 | EMS NL Madole ($M_2$) | 0.899 BCDEFG |
| 10TN-231 | EMS NL Madole ($M_2$) | 0.891 DEFG |
| 10TN-224 | EMS NL Madole ($M_2$) | 0.873 DEFG |
| 10TN-201 | EMS NL Madole ($M_2$) | 0.805 FG |
| 10TN-228 | EMS NL Madole ($M_2$) | 0.788 EFG |
| 10TN-205 | EMS NL Madole ($M_2$) | 0.779 G |

Twenty experimental dark air-cured M1 selections were evaluated against NL Madole as the control (Table 4). Thus, Table 4 shows mean Cd content in individual dark air-cured M1 breeding line selections. M1 lines with lowest and highest levels of Cd are shown in bold font; the control is shown in italics. Again, levels not connected by the same letter or symbol are significantly different. Two M1 selections accumulated significantly more Cd than control. Fourteen lines accumulated significantly less Cd than control, but not less than the GOTHIATEK® standard of 0.51.1 µg/g.

As noted herein, the tobacco plants made by the methods of the invention may comprise at least one of the 10TN-278-2, 10TN-253-4, 10TN-256-1 or 10-TN-287-4 lines described herein, wherein a representative sample of seeds for these lines are deposited with the American Type Culture Collection (ATCC, 10801 University Blvd., Manassas, Va. 20110-2209), under conditions prescribed by the Budapest Treaty, under ATCC Accession Numbers PTA-12602, PTA-12601, PTA-12599 and PTA-12600, respectively.

TABLE 4

| Entry | Pedigree/Name | Mean Cd (µg/g) |
|---|---|---|
| 10TN-253-4 | EMS NL Madole ($M_1$) | 1.494 A |
| 10TN-252-4 | EMS NL Madole ($M_1$) | 1.471 A |
| 10TN-254-4 | EMS NL Madole ($M_1$) | 1.290 B |
| *10TN-200* | *NL Madole Control* | *1.251 B* |
| 10TN-254-3 | EMS NL Madole ($M_1$) | 1.248 BC |
| 10TN-252-1 | EMS NL Madole ($M_1$) | 1.180 BCD |
| 10TN-251-1 | EMS NL Madole ($M_1$) | 1.176 BCD |
| 10TN-251_3 | EMS NL Madole ($M_1$) | 1.103 CDE |
| 10TN-252-2 | EMS NL Madole ($M_1$) | 1.072 DEF |
| 10TN-255-1 | EMS NL Madole ($M_1$) | 1.068 DEF |
| 10TN-251-2 | EMS NL Madole ($M_1$) | 1.059 DEFG |
| 10TN-255-2 | EMS NL Madole ($M_1$) | 1.003 EFGH |
| 10TN-253-1 | EMS NL Madole ($M_1$) | 1.001 EFGH |
| 10TN-256-2 | EMS NL Madole ($M_1$) | 0.932 FGHI |
| 10TN-254-2 | EMS NL Madole ($M_1$) | 0.930 FGHI |
| 10TN-257-1 | EMS NL Madole ($M_1$) | 0.912 GHI |
| 10TN-253-3 | EMS NL Madole ($M_1$) | 0.871 HI |
| 10TN-254-1 | EMS NL Madole ($M_1$) | 0.871 HI |
| 10TN-252-3 | EMS NL Madole ($M_1$) | 0.822 IJ |
| 10TN-256-1 | EMS NL Madole ($M_1$) | 0.714 J |
| 10TN-253-2 | EMS NL Madole ($M_1$) | 0.682 J |

EXAMPLE 3

Uptake and Distribution of Cd within the Tobacco Plant Mutagenesis and Breeding

Seeds from K326, a flue-cured variety, were mutagenized with EMS (ethyl methane sulfonate) essentially as described for Example 1. The M0 mutant populations were screened on tissue culture media containing 150 µM Cd. Plantlets that survived the treatment were rescued and transferred to soil. Self-seed was collected from each surviving plant in the greenhouse. This M1 seed was sown and mature transplants transplanted to the Tennessee field described in Example 2 (i.e., Table 1) known to have higher than average Cd levels. These M1 flue-cured tobacco breeding lines were evaluated and screened under field conditions at this location. Early season samples were collected from lower stalk green leaf and analyzed for Cd.

Based on early season (i.e., 65 days after transplant) heavy metal data, plants were selected for late season (i.e., 145 days after transplant) analysis to determine where the Cd was distributed, if at all. Late season samples were collected at about 145 days after transplanting from healthy plants. Lower, middle and upper lamina (no midribs) were sampled. Stalks, cut into three sections designated as lower, middle and upper, were also sampled. In addition, root and terminal bud samples were collected and analyzed for Cd content. All tissue was frozen on dry ice and freeze-dried to maintain sample integrity. Freeze-dried samples were analyzed for Cd content. Three replicates of each sample were analyzed.

Cadmium Levels as Distributed throughout the Plant:

Cadmium results from 13 early season experimental flue-cured M1 lines and K326 control are shown in Table 5. Thus, Table 5 shows Cd (pg/g) content of individual flue-cured M1 breeding line selections in plant tissue. The Limit of Quantitation (LOQ) is 100 µg/g. Levels not connected by the same letter or symbols are significantly different.

Figure 2:
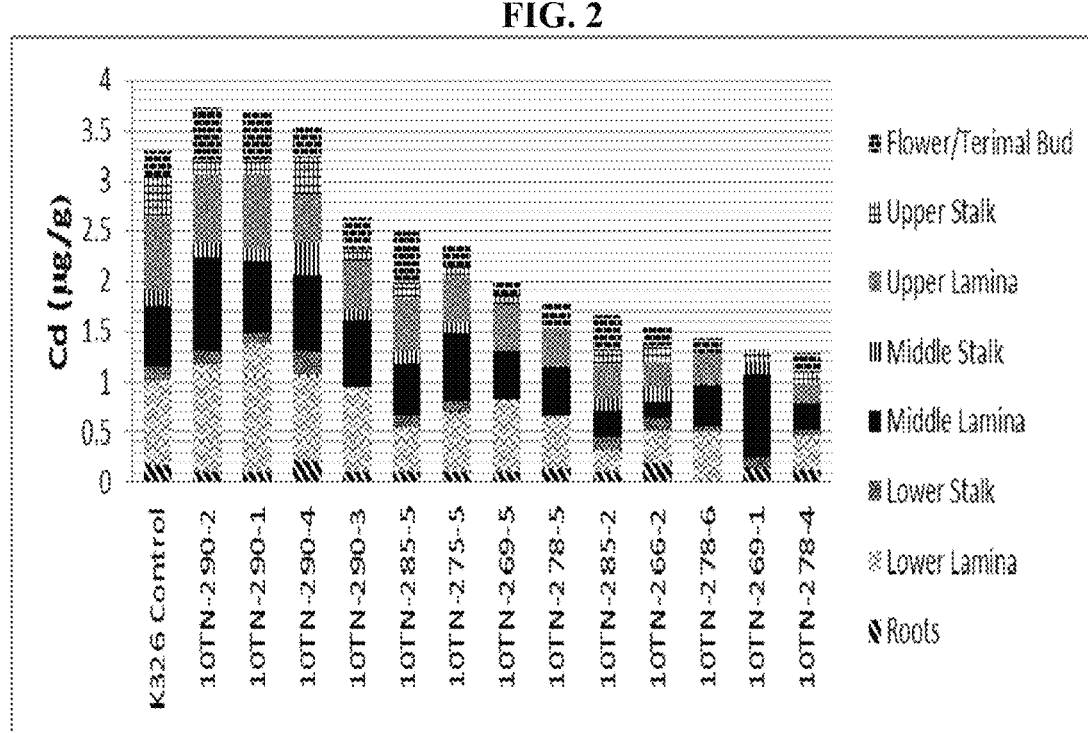
FIG. 2 shows the distribution of Cd in individual flue-cured M1 breeding line selections by plant tissue sample according to one embodiment of the invention. Bars in the graph are segmented in the order as presented in the key on the right side of the graph.

It can be seen that the K326 control accumulated the largest concentration of Cd in upper lamina. Line 10TN-290-1 accumulated the largest concentration of Cd in lower lamina tissue. Line 10TN290-2 accumulated the largest concentration of Cd in middle lamina and flower/terminal bud tissues. Line 10TN-290-4 accumulated the largest concentration of Cd in roots, lower stalk, middle stalk, and upper stalk tissues. The lowest concentration of Cd in lower lamina tissue was found in line 10TN-285-2. The lowest concentration of Cd in middle lamina tissue was found in line 10TN-266-2. The lowest concentration of Cd in upper lamina tissue was found in line 10TN-278-4. The lowest concentration of Cd in flower/terminal bud tissue was found in line 10TN-278-6. Overall, root tissue accumulated the least amount of Cd in all samples including the control, K326. FIG. 2 shows the comparison of breeding lines evaluated. It was again found that the 10TN-290 M1 lines accumulated the highest concentration of Cd compared to control.

Cd in the upper stalk position and 10TN-285-5 had the highest ratio of Cd in the flower/terminal bud tissue.

It can be seen that the 10TN-266-2 line does not move Cd from roots to above ground tissue as efficiently as other lines evaluated. This can be a desirable trait in that the leaves will have less Cd. Lines such as 10TN-290 M1, which hyper-accumulate Cd, may be used to remove Cd from the soil (i.e., for field clean-up).

Thus, these results show the ability to alter the distribution of Cd within the plant through traditional plant breeding methods.

TABLE 6

| Entry | Lower Lamina | Lower Stalk | Middle Lamina | Middle Stalk | Upper Lamina | Upper Stalk | Flower/Terminal Bud |
|---|---|---|---|---|---|---|---|
| K326 Control | 5.16 | 0.75 | 3.68 | 0.95 | 4.43 | 2.44 | 1.62 |
| 10TN-290-2 | 10.08 | 1.12 | 8.92 | 1.2 | 6.46 | 1.53 | 4.88 |
| 10TN-290-1 | 13.84 | 1.19 | 7.72 | 1.43 | 7.75 | 1.6 | 4.9 |

TABLE 5

| Entry | Roots | Lower Lamina | Lower Stalk | Middle Lamina | Middle Stalk | Upper Lamina | Upper Stalk | Flower/Terminal Bud |
|---|---|---|---|---|---|---|---|---|
| 10TN-266-2 | 0.191 AB | 0.311 FG | 0.132 B | 0.166 I | 0.155 B | 0.239 H | 0.154 B | 0.189 G |
| 10TN-269-1 | 0.133 CD | n/a | 0.117 BC | 0.805 B | 0.132 C | n/a | 0.135 CD | n/a |
| 10TN-269-5 | 0.105 DE | 0.709 CDE | <LOQ | 0.485 F | <LOQ | 0.457 DE | 0.102 FG | 0.145 H |
| 10TN-275-5 | 0.091 E | 0.593 DEF | 0.115 BC | 0.679 CD | 0.109 D | 0.445 EF | 0.121 DE | 0.222 F |
| 10TN-278-4 | 0.109 CDE | 0.348 FG | 0.054 D | 0.267 H | <LOQ | 0.215 H | 0.091 G | 0.206 FG |
| 10TN-278-5 | 0.135 C | 0.515 EF | <LOQ | 0.488 F | <LOQ | 0.410 F | <LOQ | 0.212 FG |
| 10TN-278-6 | <LOQ | 0.495 EFG | 0.053 D | 0.410 G | <LOQ | 0.329 G | <LOQ | 0.144 H |
| 10TN-285-2 | 0.100 CDE | 0.215 G | 0.124 BC | 0.268 H | 0.128 C | 0.317 G | 0.146 BC | 0.363 C |
| 10TN-285-5 | 0.102 DE | 0.439 EFG | 0.118 BC | 0.511 F | 0.127 C | 0.520 C | 0.148 BC | 0.513 A |
| 10TN-290-1 | 0.093 E | 1.287 A | 0.111 C | 0.718 CD | 0.133 C | 0.721 AB | 0.149 BC | 0.456 B |
| 10TN-290-2 | 0.106 CDE | 1.068 AB | 0.119 BC | 0.945 A | 0.127 C | 0.685 B | 0.162 B | 0.517 A |
| 10TN-290-3 | 0.093 E | 0.854 BC | n/a | 0.664 DE | 0.104 D | 0.491 CD | 0.111 EF | 0.314 D |
| 10TN-290-4 | 0.205 A | 0.848 BCD | 0.255 A | 0.748 BC | 0.321 A | 0.501 C | 0.344 A | 0.335 D |
| K326 Control | 0.165 B | 0.852 BC | 0.124 BC | 0.607 E | 0.155 B | 0.731 A | 0.157B | 0.267 E |

Table 6 shows the ratio of root to above ground tobacco tissues for Cd accumulation for late season tobacco (i.e., 145 days after transplanting) as tobacco tissue [Cd]/root [Cd]). It can be seen that when the distribution of µg Cd per gram (g) dry weight in upper tobacco tissues versus roots was expressed as a ratio, the 10TN-290-1, 10TN-290-2, and 10TN-290-3 lines had the highest ratio of Cd in all lamina positions. This suggests that these lines hyper-accumulate Cd to lamina compared to control. Conversely, 10TN-266-2 had the lowest ratio of Cd in all lamina positions even though it had a higher concentration of Cd in its roots. This suggests that the Cd is not translocated to lamina as efficiently as the 10TN-290 lines. Additionally, K326 had the highest ratio of TABLE 6-continued

| Entry | Lower Lamina | Lower Stalk | Middle Lamina | Middle Stalk | Upper Lamina | Upper Stalk | Flower/Terminal Bud |
|---|---|---|---|---|---|---|---|
| 10TN-290-4 | 4.14 | 1.24 | 3.65 | 1.57 | 2.44 | 1.68 | 1.63 |
| 10TN-290-3 | 9.18 | n/a | 7.14 | 1.12 | 5.28 | 1.19 | 3.38 |
| 10TN-285-5 | 4.3 | 1.16 | 5.01 | 1.25 | 5.1 | 1.45 | 5.03 |
| 10TN-275-5 | 6.52 | 1.26 | 7.46 | 1.2 | 4.89 | 1.33 | 2.44 |
| 10TN-269-5 | 6.75 | n/a | 4.62 | n/a | 4.35 | 0.97 | 1.38 |
| 10TN-278-5 | 3.81 | n/a | 3.61 | n/a | 3.04 | n/a | 1.57 |

TABLE 6-continued

| Entry | Lower | | Middle | | Upper | | Flower/Terminal |
| --- | --- | --- | --- | --- | --- | --- | --- |
| | Lamina | Stalk | Lamina | Stalk | Lamina | Stalk | Bud |
| 10TN-285-2 | 2.15 | 1.24 | 2.68 | 1.28 | 3.17 | 1.46 | 3.63 |
| 10TN-266-2 | 1.63 | 0.69 | 0.87 | 0.81 | 1.25 | 0.81 | 0.99 |
| 10TN-278-6 | n/a | n/a | n/a | n/a | n/a | n/a | n/a |
| 10TN-269-1 | n/a | 0.88 | 6.05 | 0.99 | n/a | 1.02 | n/a |
| 10TN-278-4 | 3.19 | 0.5 | 2.45 | n/a | 1.97 | 0.83 | 1.89 |

The root sample for 10TN-278-6 was <LOQ and therefore a ratio is not reported. The samples in bold accumulated a high ratio of Cd given availability of Cd in roots compared to K326.

Thus, EMS mutation breeding techniques were successful in identifying two flue-cured $M_1$ breeding lines that fall below the GOTHIATEK® limit for Cd. Also, in certain embodiments, genes from wild species can be introgressed into modern tobacco as an alternate genetic source for reduction in Cd uptake.

Thus, the methods of the present invention utilize a rapid and economical mutagenesis method for developing plant lines having a significantly altered uptake and/or altered levels of at least one environmental contaminant or other non-natural chemical. The alteration in uptake and/or levels may be a reduction in the uptake and/or levels of the environmental contaminant or other non-natural chemical. Or, the alteration in uptake and/or levels may be an increase in the uptake and/or levels of the environmental contaminant or other non-natural chemical. In an embodiment, the plant is tobacco. The invention provides a method whereby mutagenized tobacco seeds are allowed to germinate under selective conditions, and then chimeric plants at least partially comprising a phenotype resistant to high concentrations of cadmium or another environmental contaminant or non-natural chemical are selected.

Included in the present invention are modified tobacco lines having an alteration in a heavy metal. The heavy metal having altered uptake and/or altered levels may be at least one of arsenic (As), cadmium (Cd), chromium (Cr), nickel (Ni), lead (Pb), selenium (Se), zinc (Zn), copper (Cu), mercury (Hg) or silver (Ag). In an embodiment, the heavy metal having altered uptake and/or levels is cadmium. Or, other heavy metals and/or other selected elements may be altered. These genetically modified tobacco lines can be used as germplasm to develop new tobacco varieties with altered heavy metal profiles and/or can be mixed with other strains of tobacco to produce a blend having improved taste and aroma.

All references cited herein are incorporated by reference in their entirety.

What is claimed is:

1. A tobacco plant or portion thereof, wherein the tobacco plant is a plant of one of the 10TN-278-2, 10TN-253-4, 10TN-256-1 or 10TN-287-4 lines, representative seeds of which have been deposited under ATCC Accession Nos. PTA-12602, PTA-12601, PTA-12599 and PTA-12600, respectively.

2. A tobacco product comprising tobacco from a tobacco plant of at least one of the 10TN-278-2, 10TN-253-4, 10TN-256-1 or 10TN-287-4 lines, representative seeds of which have been deposited under ATCC Accession Nos. PTA-12602, PTA-12601, PTA-12599 and PTA-12600, respectively.

3. A composition comprising tobacco from a tobacco plant of at least-one of the 10TN-278-2, 10TN-253-4, 10TN-256-1 or 10TN-287-4 lines, representative seeds of which have been deposited under ATCC Accession Nos. PTA-12602, PTA-12601, PTA-12599 and PTA-12600, respectively.

4. The tobacco plant of claim 1, wherein the portion thereof is leaves.

5. The tobacco product of claim 2, comprising leaves of the tobacco from a tobacco plant of at least one of the 10TN-278-2, 10TN-253-4, 10TN-256-1 or 10TN-287-4 lines.

6. The tobacco product of claim 2, wherein the product is a smoking article.

7. The tobacco product of claim 6, wherein the smoking article comprises a cigarette or a cigarette component.

8. The tobacco product of claim 7, wherein the cigarette component comprises one of a smokeable material charge, a cigarette filter, or a cigarette wrapping paper.

9. The tobacco product of claim 2, wherein the product comprises a smokeless tobacco.

10. The tobacco product of claim 9, wherein the product comprises one of snuff, chewing tobacco, tobacco powder, gum, pellets, strips or tobacco formulated to be heated but not burn.

11. The tobacco composition of claim 3, comprising leaves of the tobacco from a tobacco plant of at least one of the 10TN-278-2, 10TN-253-4, 10TN-256-1 or 10TN-287-4 lines.

12. The composition of claim 11, wherein the composition is a blend of tobacco comprising leaves from a tobacco plant of at least one of the 10TN-278-2, 10TN-253-4, 10TN-256-1 or 10TN-287-4 lines.

* * * * *